US007488476B2

(12) United States Patent
Naparstek et al.

(10) Patent No.: US 7,488,476 B2
(45) Date of Patent: Feb. 10, 2009

(54) B-CELL EPITOPE PEPTIDES OF HSP 65, DNA ENCODING SAID PEPTIDES, ANTIBODIES DIRECTED AGAINST SAID PEPTIDES AND THE DIFFERENT USES THEREOF IN THE TREATMENT OF INFLAMMATORY AND AUTOIMMUNE DISEASES

(75) Inventors: Yaakov Naparstek, Jerusalem (IL); Rina Ulmansky, Mevaseret Zion (IL); Yechezkel Kashi, Haifa (IL)

(73) Assignee: Hadasit Medical Research Services & Development Ltd., Jerusalem (IL)

( * ) Notice: Subject to any disclaimer, the term of this patent is extended or adjusted under 35 U.S.C. 154(b) by 0 days.

(21) Appl. No.: 10/931,944

(22) Filed: Aug. 31, 2004

(65) Prior Publication Data

US 2005/0123535 A1 Jun. 9, 2005

Related U.S. Application Data

(63) Continuation-in-part of application No. 10/853,567, filed on May 24, 2004, now Pat. No. 7,247,305, which is a continuation of application No. 09/847,637, filed on May 2, 2001, now Pat. No. 6,770,281, which is a continuation-in-part of application No. PCT/IL99/00595, filed on Nov. 4, 1999.

(60) Provisional application No. 60/107,213, filed on Nov. 5, 1998.

(51) Int. Cl.
*A61K 39/395* (2006.01)

(52) U.S. Cl. .............. 424/139.1; 424/130.1; 424/133.1; 424/141.1; 424/150.1

(58) Field of Classification Search ........................ None
See application file for complete search history.

(56) References Cited

U.S. PATENT DOCUMENTS 5,114,844 A * 5/1992 Cohen et al. ............... 435/7.21
5,780,034 A    7/1998 Cohen et al.
5,985,287 A * 11/1999 Tan et al. ................... 424/248.1
6,770,281 B2   8/2004 Naparstek et al.

FOREIGN PATENT DOCUMENTS

WO    WO 95/25744    9/1995
WO    WO 96/10039    4/1996

OTHER PUBLICATIONS

Danieli et al., J Autoimmun. 1992, 5:443-452.*
Colman PM, Reasearch in Immunology, 1994, 145:33-36.*
Amagai, M., J. Dermatol. Sci., 1999, 20:92-102.*
Tan et al., Cutis, 2006, 3:161-165.*
Janeway et al., Immunobiology, third edition, 1997, Garland Press, pp. 11:11.*
The Merck Manual of Diagnosis and Therapy, 17th ed, editors Beers & Berkow, Merck Research laboratories, 1999, pp. 165-177, 409-423, 445-447, 449-451, 455-459, and 2041-2045.*
Wicker et al., Journal of Autoimmunity, 2005, 25:29-33.*
Young, MF, Trends Pharmacol. Sci., 2005, 26:333-335.*
Noerager et al., J Neuroimmunol. 2001, 113:163-169.*
Mason et al., Osteoarthritis and Cartilage, 2001, 9:85-91.*
Ameye et al., Curr Opin Rheumatol. 2006, 8:537-47.*
Van de Berg, WB, Curr Opin Rheumatol., 2001, 13:452-6.*
Steinberg et al., J. Autoimmun., 1992, 5 Suppl A:197-203, abstract only.*
Anderton et al., "Inflammation activates self hsp60-specific T. cells", Eur. J. Immuno., 23:33-38, 1993.
Anderton et al., "Activation of T Cells Recognizing Self 60-kD Heat Shock Protein Can Protect against Experimental Arthritis", J. Exp. Med., 181:943-952, 1995.
Anderton et al, "Differential mycobacterial 65-kDa Heat Shock Protein T. Cell Epitope Recognition after Adjuvant Arthritis-Inducing or Protective immunization Protocols", Journal of Immunology, 152:3656-3664, 1994.
Barker et al., "Differential Effects of Immunization with Mycobacterial 65 kD Heal Shock Protein on Two Models of Autoimmunity", Immunity, 14:73-77, 1992.
Billingham et al. "A Mycobacterial 65-kD heat Shock Protein Induces Antigen-Specific Suppression Of Adjuvant Arthritis, But Is Not Itself Arthritogenic", J. Exp. Med. 171:339-344, 1990.
Chen et al., "Human 60-kDa Heat-Shock Protein: A Danger Signal to the Innale Immune System", The Journal of Immunology, 162:3212-3219, 1999.

(Continued)

*Primary Examiner*—Michael Szperka
(74) *Attorney, Agent, or Firm*—Martin Fleit; Paul D. Bianco; Fleit Gibbons Gutman Bongini & Bianco PL

(57) ABSTRACT

B-cell epitope peptides of HSP 65, particularly the peptides comprising the amino acid sequence substantially as denoted by SEQ ID: Nos. 1-5 and their biologically functional homologues and derivatives thereof. Also included are polyclonal and monoclonal antibodies directed against them and their compositions for passive immunization against inflammatory and autoimmune diseases and in the treatment of inflammatory and autoimmune diseases. Also encompassed are diagnostic uses of these antibodies, for identifying people at risk of developing arthritis or diabetes, and a method of monitoring progress of the disease conditions and disease prognosis.

13 Claims, 12 Drawing Sheets

OTHER PUBLICATIONS

Elias, D. and Cohen, IR, "The hsp60 Peptide p277 Arrests the Autoimmune Diabetes Induced by the Toxin Streptozotocin" Diabetes, 45:1168-1172, 1996.

Elais, D. and Cohen, IR, "Peptide therapy for diatetes in NOD mice", The Lancet, 343:704-706, 1994.

Friedland et al, "Mycobacterial 65-kD heat shcok protein induces release of proinflammatory cytokines from human monocytic cell", Clin Exp. Immunol, 91:58-62, 1993.

Ghoraishian et al, "Comparison between the protective effects of mycobacterial 65-kD heat shock protein and ovomucoid in pristane-induced arthritis: relationship with agalactosyl IgG", Clin. Exp. Immunol., 94:247-251, 1993.

Griffiths et al., "Induction of Autoimmune Arthritis in Rats by Immunization with Homologous Rat Type II Collagen is Restricted to the RT1av1 Haplotype", Arthritis and Rheumatism, 36(2):254-258, 1993.

Henwood et al, "Restricted T Cell receptor expression by human T cell clones specific for mycoobacterial 65-kDa heat-shock protein: selective in vivo expansion of T cells bearing defined receptors", Eur. J. Immunol., 23:1256-1265, 1993.

Hill Gaston et al, "Recognition of a mycobacteria-Specific Epitope in the 65 kD Heat-Shock Protein by Synovial Fluid-Derived T Cell Clones", J. Exp. Med., 171:831-841, 1990.

Hill Gaston et al, "In Vitro Responses to a 65-Kilodalton Mycobacterial Proteins by Synovial T. Cells from Inflammatory Arthritis Patients", The Journal of Immunology, 143(8):2494-2500, 1989.

Hogervorst et al, "Modulation of Experimental Autoimmunity: Treatment of Adjuvant Arthritis by Immunization with a Recombinat Vaccinia Virus". Infection and Immunity, 59(6):2029-2035, 1991.

Hogervorst et al., "T cell reactivity to an epitope of the mycobacterial 65-kDa heat-shock protein (hsp 65) corresponds with arthritis susceptibility in rats and is regulated by hsp 65-specific cellular responses", J. Immunol. 21:1296, 1991.

Holoshitz et al., T Lymphocytes of Rheumatoid Arthritis Patients Show Augmented Reactivity to a Fraction of Mycobateria Cross-Reactive with Cartilage, The Lancet, 305-309, 1986.

Holoshitz et al, "Lines of T Lymphocytes Induce or Vaccinate Against Autoimmune Arthritis" Science, 219:56-58. 1983.

Jindal et al, "Primary Structure of a Human Mitochondrial Protein Homologous to the Bacterial and Plant Chaperonins and to the 65-Kilodalton mycobacterial Antigen", Molecular and Cellular Biology, 9 (5):2279-2283. 1989.

Jordan, SC and Toyoda, M, "Treatment of autoimmune diseases and systemic vasculitis with pooled human intravenous immune globulin", Clin. Exp. Immunol., 97(1):31-38, 1994.

Kasprzyk et al, "Solid-Phase peptide Quantitation Assay Using Labeled Monoclonal Antibody and Glutaraldehyde Fixation", Analytic Biochemistry, 174:224-234, 1988.

Kleinau et al, "A Monoclonal Antibody to the Mycobaterial 65kDa Heat Shock Protein (ML 30) Binds to Cells in Normal and Arthritic Joints of Rats". Scand. J. Immunol., 33:195-202, 1991.

Lopez-Mortalla et al, "A common structural motif in immunopotentiating peptides with sequences present in human autoantigens. Elicitation of a response mediated by monocytes and Th 1 cells", Biochemica et Biophysica Acta. 1317:183-191. 1996.

Maloy et al, "Production of Antipeptide Antisera", Current Protocols in Immunology, 39:9.4-9.4.12, 2000.

Margulies. DH, "Antibody Detection and Preparation", Current Protocols in Immunology, 2.01-1.13.16, 1996.

Moudgil et al., "Diversification of T Cell Responses to Carboxy-terminal Determinants within the 65-kD Heat-Shock Protein is Involved in Regulation of Autoimmune Arthritis", J. Exp. Med., 185(7):1307-1316, 1997.

Munk et al., "T Lymphocytes from Healthy Individuals with Specificity to Self-Epitopes Shared by the Mycobacterial And Human 65-Kilodalton Heat Shock Protein", The Journal of Immunology, 143(9):2844-2849, 1989.

Pearson, Carl M., "Development of Arthritis, periarthritis and Periostitis in Rats Given Adjuvants", Proc. Soc. Exp. Biol. Med. 91:95-100 (1956).

Pearson, Carl M. and Wood, Fac D., "Studies of Polyarthritis and Other Lesions Induced in Rats by Injection of Mycobacterial Adjuvant. I. General Clinical and Pathologic Characteristics and Some Modifying Factors", Arthritic Lesions from Mycobacteria, 2:440-450 (1956).

Prakken et al., "Nasal administration of arthritis-related T cell epitopes of heat shock protein 60 as a promising way for immunotherapy in chronic arthritis", Biotheraphy, 10:205-211, 1998.

Prakken et al, "Peptide-induced nasal tolerance for a mycobacterial heat shock protein 60 T cell epitope in rats suppresses both adjuvant arthritis and nonmicrobially induced experimental arthritis", Proc. Natl. Acad. Sci. USA, 94:3284-3289, 1997.

Quayle et al, "peptide recognition, T cell receptor usage and HLA restriction elements of human heat-shcok protein (hsp) 60 and mycobacterial 65-kDa hsp-reactive T cell clones from rheumatoid synovial fluid", Eur. J. Immunol., 22:1315-1322, 1992.

Res et al., "Synovial Fluid T Cell Reactivity Against 65 kD Heat Shock Protein of Mycobacteria in Early Chronic Arthritis". The Lancet, 478-480, 1988.

Ulmansky, R. and Naparstek, Y., "Immunoglobulins from rats that are resistant to adjuvanl arthritis suppress the disease in arthritis-susceptible rats", Eur. J. Immunol, 25:952-957, 1995.

Van Eden et al., "Cloning of the mycobacterial epotope recognized by T lymphocytes in adjuvant arthritis". Nature, 331:171-173, 1988.

Waksman. BH and Wennersten, C, Passive Transfer of Adjuvant Arthritis in Rats with Living Lymphoid Cells of Sensitized Donors, Int. Arch. Allergy, 23(3-4); 129-139, 1963.

Warren et al, "Fine Specificity of the antibody response to myelin basic protein in the central nervous system in multiple selerosis: The minimal B-cell epitope and a model of its features", Proc. Natl. Acad. Sci. USA, 92:11061-11065, 1995.

Yang et al., Prevention of adjuvant arthritis in rats by a nonapeptide from the 65-kD mycobacterial heat-shock protein, Clin Exp. Immunol., 81:189-194, 1990.

Yang et al, "Treatment of Adjuvant Arthritis in Rats: Vaccination Potential of a Synthetic Nonapeptide from the 65 kDa Heat Shock Protein of Mycobacterial", Journal of Autoimmunity. 3:11-23, 1990.

Lederman et al. Molecular Immunology, vol. 28, No. 11, pp. 1171-1181 (1991).

Hogervorst et al., Adjuvant arthritis and immunity to the mycobacterial 65 kDa heat shock protein, International Immunology, 4(7):719-727, 1992.

Li et al, Proc. Natl. Acad. Sci.USA, vol. 77, No. 6, pp. 3211-3214, (1980).

Van Regenmortel Marc H.V., Methods: "A Companion to Methods of Enzymology", vol. 9, pp. 465-472, (1996).

M. Steinitz, Human Monoclonal Antibodies Produced by Epstein-Barr Virus Immortalized Cell Lines: Technical and Theoretical Principles, Monoclonal Antibodies from EBV Immortalized Cell Lines, 1988, vol. 2.

Rina Ulmansky, Resistance to Adjuvant Arthritis Is Due to Protective Antibodies Against Heat Shock Protein Surface Epitopes and the Induction of IL-10 Secretion, The Journal of Immunology, 2002, 168:6463-6469.

Wright, HT, 1991, Crit Rev Biochem Mol Biol. 26:1-52.

McKerrow, JH, 1979, Mech Ageing Dev 10:371-377.

World wide web.infoplease.com/dictionary/immunity, downloaded Mar. 23, 2006, 2 pages.

World wide web.onelook.com/?other=web1931&w=Immunity, downloaded Mar. 23, 2006, one page.

Stryer, L. Biochemistrys, 4th edition, W.H. Freeman & Co. 1995, pp. 53-58.

"Amino Acid Side Chain Modification Agents", downloaded from piercenet.com on Mar. 24, 2006, 2 pages.

"Protein Modification Reagents", downloaded from piercenet.com on Mar. 24, 2006 4 pages.

"Cross-Linking", downloaded from piercenet.com on Mar. 24, 2006, 10 pages.

"Crosslinking Reagents", downloaded from piercenet.com on Mar. 24, 2006, 2 pages.

The Merck Manual of Diagnosis and Therapy, 17th edition, 1999, editors Beers and Berkow, Merck Research Laboratories, pp. 96-99, 1290-1925, and 1474-1477.

Colman, P.M., 1994, Research in Immunology, 145:33-36.

Lopez-Guerrero et al., 1993, Infection and Immunity, 61:4225-4231.

The Merck Manual of Diagnosis and therapy, 17th edition, Merck Research Laboratories, 1999, pp. 416-423, 922-925, and 1496-1499.

Astarloa et al., J. Neurological Sci4ences, 1996 135:182-183.

Xiao et al., BMC Blood Disorders, 2004, 4:1, 10 pages.

Janeway et al., Immunobiology, 3rd edition, Garland Publishing Inc, 1997, pp. 8:2-8:7.

Prakken et al., "Heat Shock Protein 60 and adjuvant arthritis: a model for T cell regulation in human arthritis", Springer Seminars in Immunology, (2003) 25: 47-63.

Myers et al., "Collagen-Induced Arthitis, an animal model of autoimmunity", Life Sciences, vol. 61, No. 19, p. 1861-1878 (1997).

Brand et al., "Immunopathogenesis of Collagen Arthritis", Springer Seminars in Immunopathology, Spring 2003, 25: 3-18.

Bongartz et al., "Treatment of active psoriatic arthritis with the PPAR gamma ligand pioglitazone: an open-label pilot study", Thuematology, vol. 44, No. 1, 2004.

Holoshitz et al, Lines of T Lymphocytes Induce or Vaccinate Against Autoimmune Arthritis, Science, 219:56-58 (1983).

\* cited by examiner

|  |  |  | 1 | 6 | 25 |
|---|---|---|---|---|---|
| HSP 65 - *M.T.* | ---------- | ---------- | -----MAKTI | AYDEEARRGL | ERGLNALADA |
| HSP 60 - *RAT* | MLRLPTVLRQ | MRPVSRALAP | HLTRAYAKDV | KFGADARALM | LQGVDLLADA |
| HSP 60 - *HUMAN* | MLRLPTVFRQ | MRPVSRVLAP | HLTRAYAKDV | KFGADARALM | LQGVDLLADA |
| Consensus | ---------- | ---------- | ------AK-- | -----AR--- | --G---LADA |

|  | 26 |  |  |  | 75 |
|---|---|---|---|---|---|
| HSP 65 - *M.T.* | VKVTLGPKGR | NVVLEKKWGA | PTITNDGVSI | AKEIELEDPY | EKIGAELVKE |
| HSP 60 - *RAT* | VAVTMGPKGR | TVIIEQSWGS | PKVTKDGVTV | AKSIDLKDKY | KNIGAKLVQD |
| HSP 60 - *HUMAN* | VAVTMGPKGR | TVIIEQSWGS | PKVTKDGVTV | AKSIDLKDKY | KNIGAKLVQD |
| Consensus | V-VT-GPKGR | -V---E--WG- | P--T-DGV-- | AK-I-L-D-Y | --IGA-LV-- |

6-7(31-52 AA)

|  | 76 |  |  |  | 125 |
|---|---|---|---|---|---|
| HSP 65 - *M.T.* | VAKKTDDVAG | DGTTTATVLA | QALVREGLRN | VAAGANPLGL | KRGIEKAVEK |
| HSP 60 - *RAT* | VANNTNEEAG | DGTTTATVLA | RSIAKEGFEK | ISKGANPVEI | RRGVMLAVDA |
| HSP 60 - *HUMAN* | VANNTNEEAG | DGTTTATVLA | RSIAKEGFEK | ISKGANPVEI | RRGVMLAVDA |
| Consensus | VA--T---AG | DGTTTATVLA | -----EG--- | ---GANP--- | -RG---AV-- |

21 (121-136 AA)

|  | 126 |  |  |  | 174 |
|---|---|---|---|---|---|
| HSP 65 - *M.T.* | VTETLLKGAK | EVETKEQIAA | TAAISA.GDQ | SIGDLIAEAM | DKVGNEGVIT |
| HSP 60 - *RAT* | VIAELKKQSK | PVTTPEEIAQ | VATISANGDK | DIGNIISDAM | KKVGRKGVIT |
| HSP 60 - *HUMAN* | VIAELKKQSK | PVTTPEEIAQ | VATISANGDK | EIGNIISDAM | KKVGRKGVIT |
| Consensus | V---L-K-- | -V-T-E-IA- | -A-ISA-GD- | -IG--I---AM | -KVG--GVIT |

|  | 175 |  |  |  | 224 |
|---|---|---|---|---|---|
| HSP 65 - *M.T.* | VEESNTFGLQ | LELTEGMRFD | KGYISGYFVT | DPERQEAVLE | DPYILLVSSK |
| HSP 60 - *RAT* | VKDGKTLNDE | LEIIEGMKFD | RGYISPYFIN | TSKGQKCEFQ | DAYVLLSEKK |
| HSP 60 - *HUMAN* | VKDGKTLNDE | LEIIEGMKFD | RGYISPYFIN | TSKGQKCEFQ | DAYVLLSEKK |
| Consensus | V----T---- | LE--EGM-FD | -GYIS-YF-- | ----Q----- | D-Y-LL---K |

31 (181-196 AA)   36 (211-226 AA)

|  | 225 |  |  |  | 274 |
|---|---|---|---|---|---|
| HSP 65 - *M.T.* | VSTVKDLLPL | LEKVIGAGKP | LLIIAEDVEG | EALSTLVVNK | IRGTFKSVAV |
| HSP 60 - *RAT* | ISSVQSIVPA | LEIANAHRKP | LVIIAEDVDG | EALSTLVLNR | LKVGLQVVAV |
| HSP 60 - *HUMAN* | ISSIQSIVPA | LEIANAHRKP | LVIIAEDVDG | EALSTLVLNR | LKVGLQVVAV |
| Consensus | -S------P- | LE------KP | L-IIAEDV-G | EALSTLV-N- | -------VAV |

```
              275                                                            323
HSP 65 - M.T. KAPGFGDRRK  AMLQDMAILT  GGQVISEE.V  GLTLENADLS  LLGKARKVVV
HSP 60 - RAT  KAPGFGDNRK  NQLKDMAIAT  GGAVFGEEGL  NLNLEDVQAH  DLGKVGEVIV
HSP 60 - HUMAN KAPGFGDNRK NQLKDMAIAT  GGAVFGEEGL  TLNLEDVQPH  DLGKVGEVIV

Consensus     KAPGFGD-RK  --L-DMAI-T  GG-V--EE--  -L-LE-----  -LGK---V-V 324                                                            373
HSP 65 - M.T. TKDETTIVEG  AGDTDAIAGR  VAQIRQEIEN  SDSDYDREKL  QERLAKLAGG
HSP 60 - RAT  TKDDAMLLKG  KGDKAHIEKR  IQEITEQLDI  TTSEYEKEKL  NERLAKLSDG
HSP 60 - HUMAN TKDDAMLLKG KGDKAQIEKR  IQEIIEQLDV  TTSEYEKEKL  NERLAKLSDG Consensus     TKD------G  -GD---I--R  ---I------  --S-Y--EKL  -ERLAKL--G
                                                 59 (349-364 AA)

374                                                            423
HSP 65 - M.T. VAVIKAGAAT  EVELKERKHR  IEDAVRNAKA  AVEEGIVAGG  GVTLLQAAPT
HSP 60 - RAT  VAVLKVGGTS  DVEVNEKKDR  VTDALNATRA  AVEEGIVLGG  GCALLRCIPA
HSP 60 - HUMAN VAVLKVGGTS DVEVNEKKDR  VTDALNATRA  AVEEGIVLGG  GCALLRCIPA

Consensus     VAV-K-G---  -VE--E-K-R  --DA-----A  AVEEGIV-GG  G--LL---P-
              63 (373-388 AA)

424                                                            472
HSP 65 - M.T. LDELK.LEGD  EATGANIVKV  ALEAPLKQIA  FNSGLEPGVV  AEKVRNLPAG
HSP 60 - RAT  LDSLKPANED  QKIGIEIIKR  ALKIPAMTIA  KNAGVEGSLI  VEKILQSSSE
HSP 60 - HUMAN LDSLTPANED QKIGIEIIKR  TLKIPAMTIA  KNAGVEGSLI  VEKIMQSSSE

Consensus     LD-L-----D  ---G--I-K-  -L--P---IA  -N-G-E----  -EK-------

473                                                            522
HSP 65 - M.T. HGLNAQTGVY  EDLLAAGVAD  PVKVTRSALQ  NAASIAGLFL  TTEAVVADKP
HSP 60 - RAT  VGYDAMLGDF  VNMVEKGIID  PTKVVRTALL  DAAGVAPLLT  TAEAVVTEIP
HSP 60 - HUMAN VGYDAMAGDF VNMVEKGIID  PTKVVRTALL  DAAGVASLLT  TAEVVVTEIP

Consensus     -G--A--G--  ------G--D  P-KV-R-AL-  -AA--A-L--  T-E-VV---P
                                                 84 (499-514 AA)

523         540
HSP 65 - M.T. EKEKASVPGG  GDMGGMDF--  -----
HSP 60 - RAT  KEEKD..PGM  GAMGGMGGGM  GGGMF
HSP 60 - HUMAN KEEKD..PGM GAMGGMGGGM  GGGMF

Consensus     --EK---PG-  G-MGGM----  -----
```

Fig. 1 (continued)

The "Protective" Motif

MT  HSP Peptide 6- (31-46)   G P K G R N V V L E K K W G A P

MT  HSP Peptide 7- (37-52)           V V L E K K W G A P T I T N D G

Rat HSP Peptide 5- (36-55)              T V I I E Q S W G S P K V T K D G V T V

Common Motif                    V = = E - - W G - P

Fig. 5

B-CELL EPITOPE PEPTIDES OF HSP 65, DNA ENCODING SAID PEPTIDES, ANTIBODIES DIRECTED AGAINST SAID PEPTIDES AND THE DIFFERENT USES THEREOF IN THE TREATMENT OF INFLAMMATORY AND AUTOIMMUNE DISEASES

RELATED CASES

This application is a continuation-in-part of application Ser. No. 10/853,567, filed May 24, 2004, which is a continuation of application Ser. No. 09/847,637, filed May 2, 2001, now U.S. Pat. No. 6,770,281 B2, which is a continuation-in-part of Intl. application Ser. No. PCT/IL99/00595, filed Nov. 4, 1999, claiming priority of Provisional. Appl. No. 60/107,213, filed Nov. 5, 1998, the contents of all named related cases being here incorporated by reference in their entirety.

FIELD OF THE INVENTION

The present invention relates to various peptides, homologous to regions of heat shock protein (HSP), to DNA sequences encoding such peptides, to DNA constructs comprising the DNA sequences, to antibodies directed against peptides of the invention. The invention also relates to active vaccines comprising the said peptides, a DNA sequence encoding a peptide of the invention, and to a passive immunization composition comprising at least one antibody of the invention.

BACKGROUND OF THE INVENTION

Throughout this application, various publications are referred to by Arabic numerals in parentheses. These publications are incorporated herein in their entireties and constitute part of the description.

Adjuvant Arthritis (AA) is an experimental model of autoimmune arthritis which can be induced in susceptible strains of rats such as inbred Lewis or Wistar strains upon vaccination with heat-killed *Mycobacterium tuberculosis* (MT) in complete Freund's Adjuvant (CFA) [1-3]. The disease cannot be induced in resistant strains of rats (e.g., Brown-Norway; Fisher [5,6], and Lewis rats develop resistance to re-induction of the disease after recovery from arthritis.

The inventors have previously shown that resistance to AA can be transferred to a susceptible strain of rats by intravenous infusion of immunoglobulins from resistant strains, and that resistance is associated with the presence of antibodies against the 65 KD MT heat shock protein (HSP 65) [4].

Heat shock proteins are a family of highly conserved proteins. There is ~50% amino acid identity between the Mycobacterial HSP 65 and the mammalian HSP 60 [21]. The role of the 65 KD heat shock protein (HSP 65) of MT in the pathogenesis of autoimmune arthritis, both in experimental animals [7, 8] as well as in humans [9-11], has been investigated intensively in the past several years. For example, Barker et al. [32] describe the suppression of arthritogenic immune responses in mice given HSP 65 and pristane. The antigen used to elicit the response was full-length HSP 65, and no attempt was made to investigate the effect of specific sub-domains or peptides deriving from this protein.

AA can be passively transferred by a T-cell clone reactive to residues 180-188 of the MT HSP 65, and in patients suffering from rheumatoid arthritis (RA), an association between T-cell responses to HSP 65 and early stages of joint inflammation has been found [7, 12-14]. Paradoxically, pre-immunization with the mycobacterial HSP 65 leads to resistance to induction of the disease by MT and this protective effect is believed to be mediated by T cells specific for HSP 65 [7, 15-16]. Likewise, although arthritic rats develop vigorous T cell responses to self-HSP and to peptide 180-188 of the MT HSP, neither of these is arthritogenic when injected to arthritis-susceptible rats [15, 17]. These results and other suggest that HSP may contain epitopes that are disease-related and other epitopes that confer resistance [5, 19, 20]. Both the pathogenic immune response as well as the protective effect were attributed to anti-HSP T-cells. The examples of the present application illustrate the fine epitope specificity of the anti-HSP antibodies of arthritis-susceptible and resistant rats.

In addition, the inventors have found that naive Lewis rats lack antibodies to certain epitopes of the mycobacterial HSP 65 which are found naturally in young BN and old naive Lewis rats, and that are acquired by young Lewis rats after recovery from the disease. Analysis of the primary and tertiary structure of the whole MT HSP 65 KD molecule indicated that these "protective" epitopes are potential B-cell epitopes with a non-conserved amino acid sequences that are found on the outer surface of the molecule.

Pre-immunization of Lewis rats with one of the "protective" epitopes prior to induction of the disease induced antibodies against the whole molecule as well as resistance to disease induction. This peptide (SEQ ID: No. 2) corresponds also to the self-HSP 60 epitope to which antibodies were found in the arthritis resistant rats, but not in the arthritis-susceptible naive Lewis rats.

SUMMARY OF THE INVENTION

The present invention relates to a peptide comprising the amino acid sequence substantially as denoted by SEQ ID: No. 1 and biologically functional homologues and derivatives thereof.

More particularly, the invention relates to a peptide having the amino acid sequence substantially as denoted by SEQ ID: No. 2 and biologically functional homologues and derivatives thereof and to a peptide having the amino acid sequence substantially as denoted by SEQ ID: No. 3 and biologically functional homologues and derivatives thereof.

In addition, the invention relates to a peptide comprising the amino acid sequence substantially as denoted by SEQ ID: No. 4 and biologically functional homologues and derivatives thereof.

The peptides of the invention can be synthetic peptides and chemically modified peptides.

The peptides of the invention are capable of conferring immunity against autoimmune and/or inflammatory disorders.

In a further aspect, the invention relates to a nucleic acid sequence encoding a peptide of the invention and to DNA constructs comprising the same.

In yet a further aspect, the invention relates to vaccines comprising as active ingredient an effective vaccinating amount of at least one peptide of the invention, or a nucleic acid according to the invention. The vaccines of the invention are particularly useful in conferring immunity against autoimmune or inflammatory disorders.

Still further, the invention relates to antibodies directed against the peptides of the invention and to compositions comprising them. The compositions of the invention are particularly useful for the passive vaccination against autoimmune or inflammatory disorders.

In addition, the invention also relates to new methods for diagnosis, prevention and treatment of inflammatory and autoimmune disorders.

DESCRIPTION OF THE FIGURES

FIG. 1 Amino Acid Comparison of Three HSP 60 Sequences

*Mycobacterium Tuberculosis*, rat HSP 60 and human HSP 60 (reference sequences P06806, P19227 and P10809, corresponding to SEQ ID: Nos. 6, 7 and 8 respectively), were compared with pileup program from GCG-Wisconsin Package v9.0. The conserved regions are indicated (consensus). Bold, underlined residues represent the preferred peptides.

Figure 2:
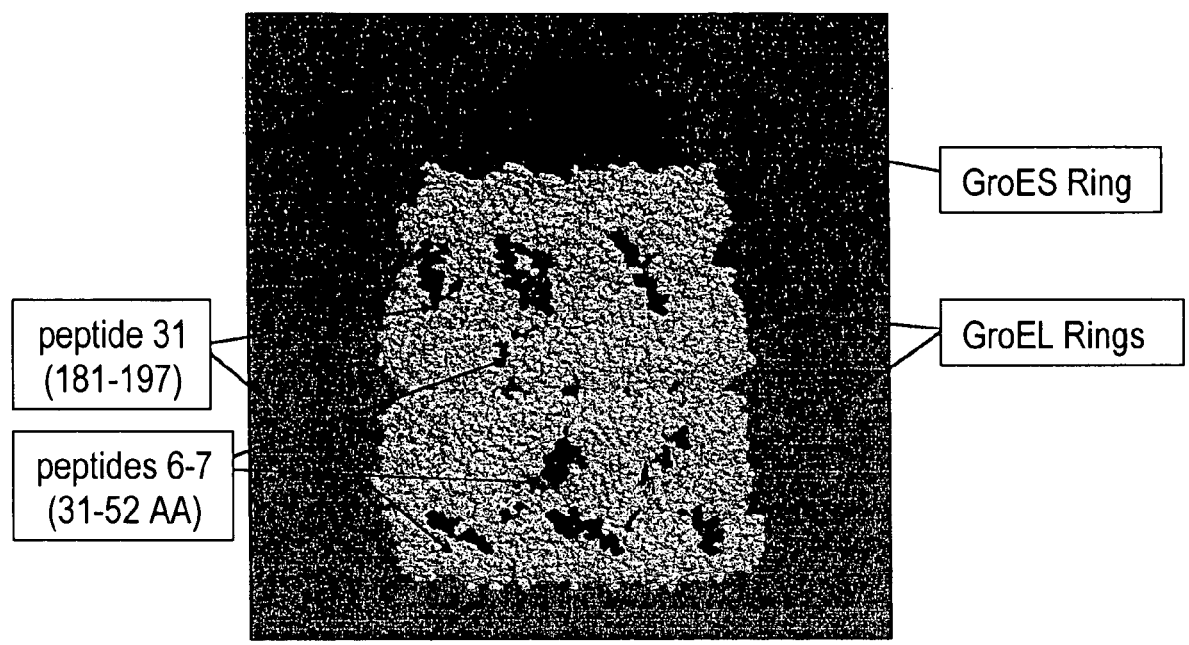

FIG. 2 Three Dimensional Structure of the *E. coli* GroEL-GroES Complex

The GroES heptameric ring is shown in dark gray. The two GroEL heptameric rings are shown in light gray. Peptides 6-7 (amino acids 31-52) and 31 (amino acids 181-197) are also indicated.

Figure 3A:
Figure 3B:
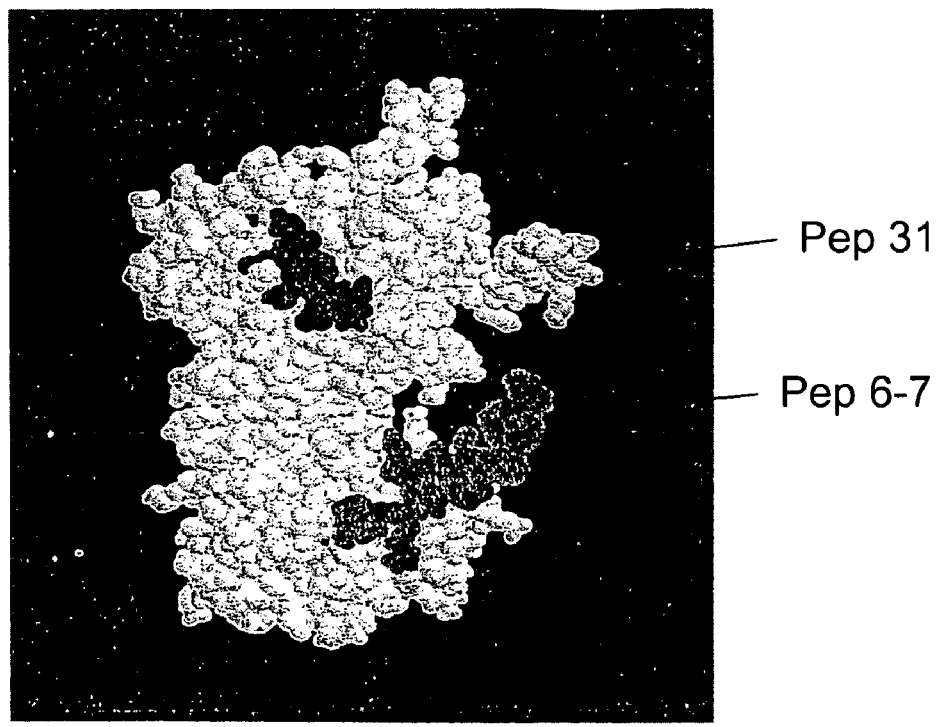

FIGS. 3a-3b The Location of Peptides 6, 7 and 31 in the HSP 65 Monomer

The location of peptides 6, 7 and 31 in the HSP 65 monomer is indicated in a secondary structure configuration (FIG. 3a) and in the space filling mode (FIG. 3b).

Figure 4:
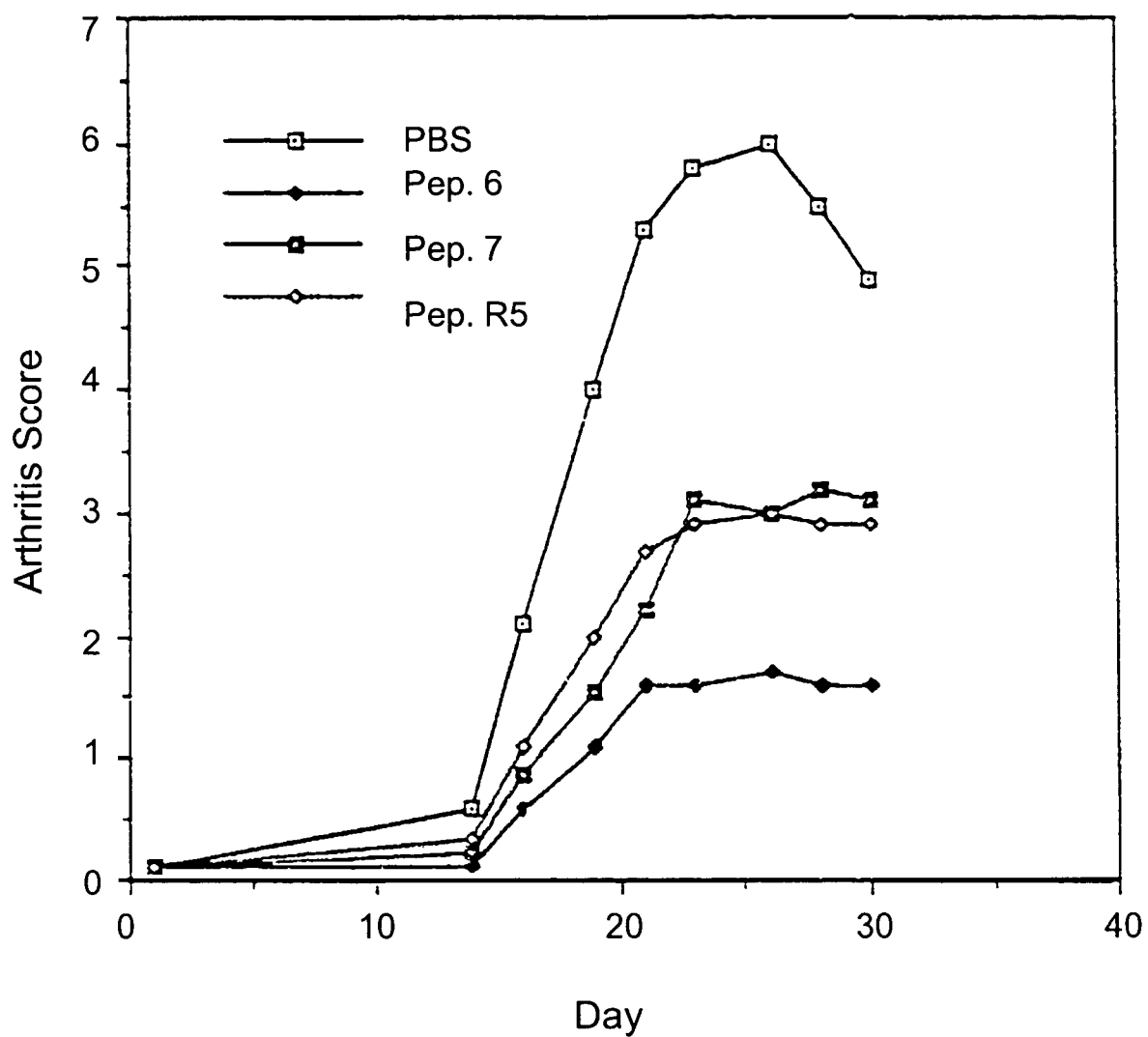

FIG. 4 AA Development in Lewis Rats After Vaccination with HSP Peptides

Measurement of AA disease score in Lewis rat immunized with HSP peptides 6, 7 and R5 prior to AA induction. PBS was used as control.

FIG. 5 The protecting motif within peptides 6, 7 and R5

A common motif within peptides 6, 7 and R5, V—E—WG-P (also denoted by SEQ ID NO: 9) is shown.

Figure 6:
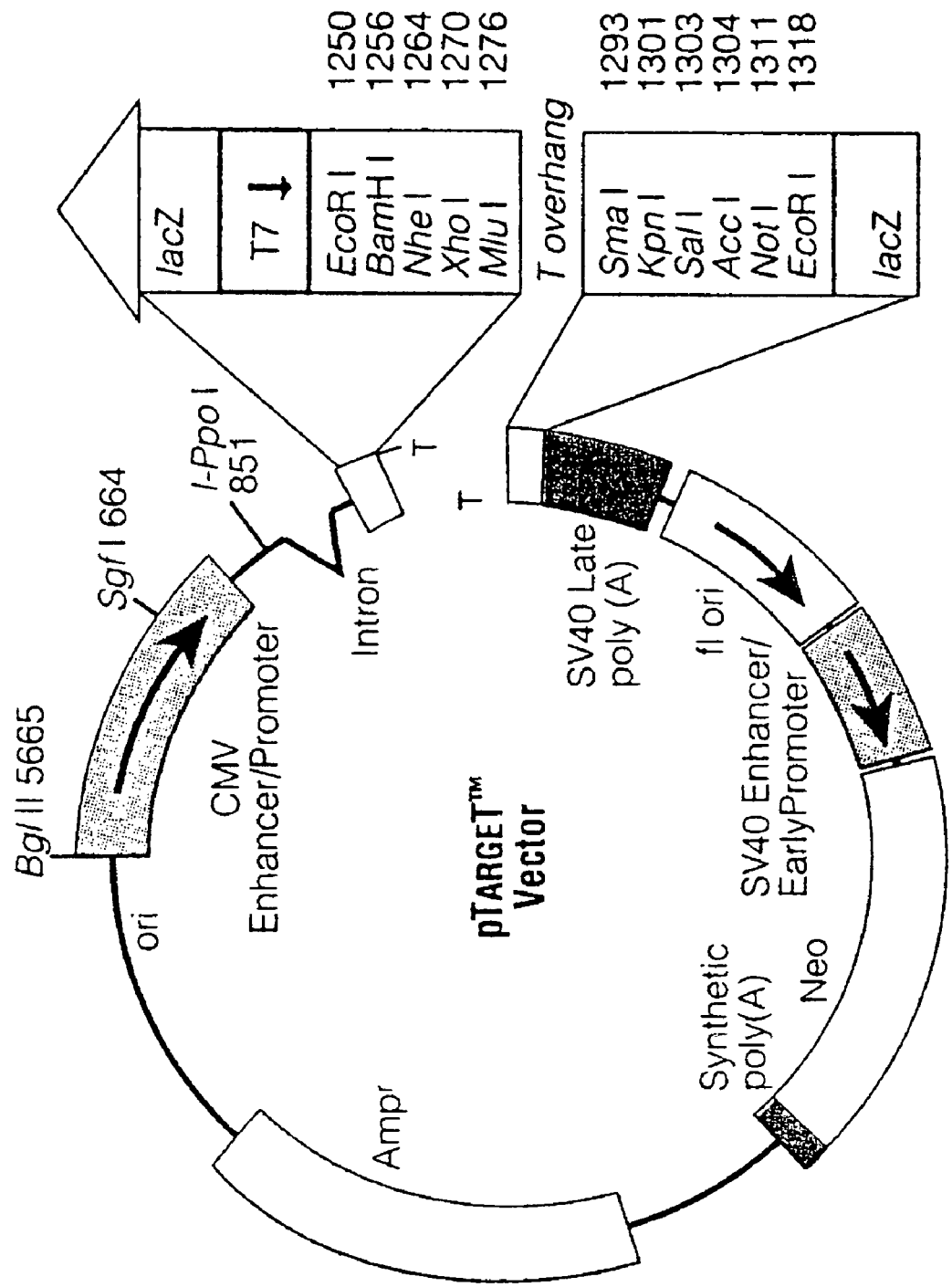

FIG. 6 pTARGET Plasmid Map

Description map of the pTARGET plasmid is shown.

Figure 7:
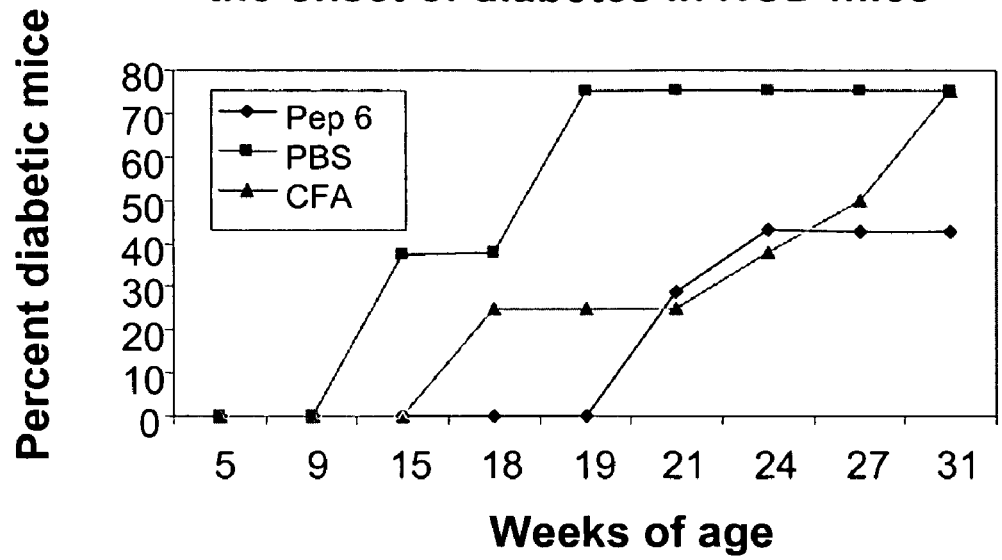

FIG. 7 Effect of Peptide 6 Immunization on the Onset of Diabetes in NOD Mice

Naive NOD mice were immunized 3 times intradermally (I.D.) with 100 μg peptide 6 (SEQ ID: No. 2) in CFA and IFA. Control mice received PBS. Mice were monitored for the onset of diabetes by glucose test and for anti-peptide 6 or anti-HSP 65 antibodies by ELISA. Mice immunized with the peptide developed anti-peptide 6 as well as anti-HSP 65 antibodies as detected by OD (1.52±0.07 and 1.43±0.13 respectively) in comparison to CFA immunized mice (0.05±0.01 and 0.01±0.01) and control mice (0.09±0.06 and 0.16±0.16).

Figure 8:
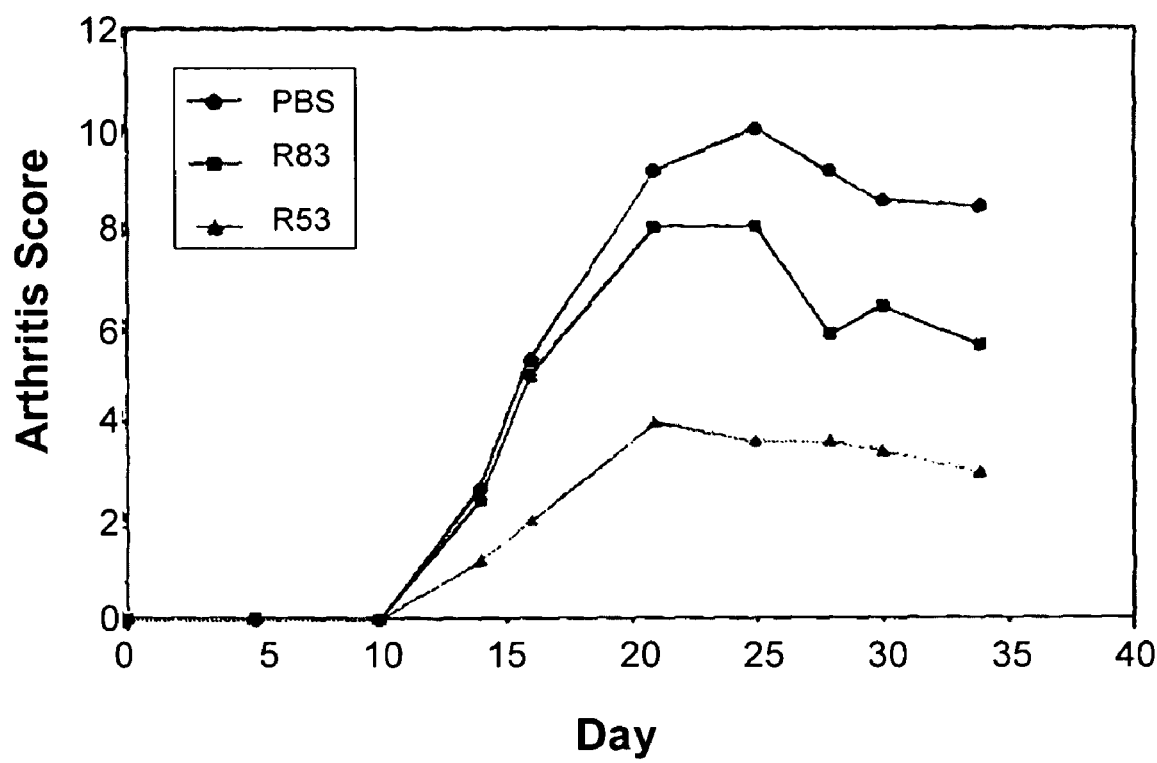

FIG. 8 Modulation of AA by Rat Anti-Peptide 6 Monoclonal Antibody R53F

Lewis rats were immunized with MT in CFA and treated with the monoclonal rat anti-peptide 6 R53F immunoglobulin, a control rat monoclonal antibody R83D or PBS. Two injections were given, the first intravenously (I.V.) and the second intraperitoneally (I.P.). Disease severity was evaluated every other day. Arthritis score expresses the mean result of 5 animals. *p<0.05 compared to PBS treated rats.

Figure 9:
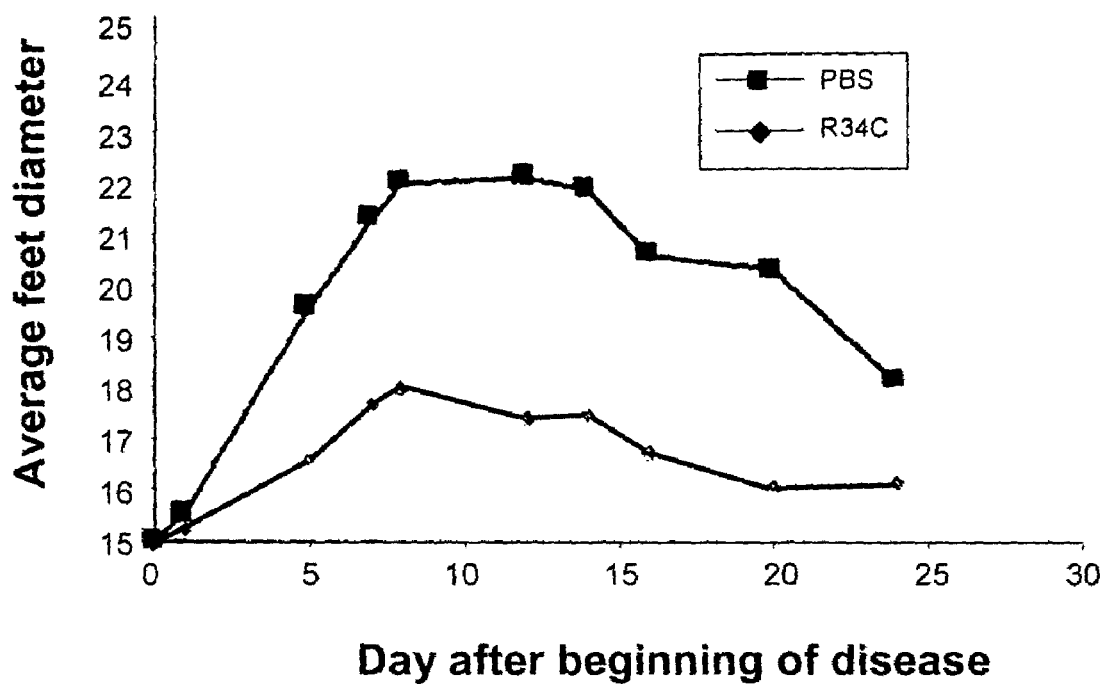

FIG. 9 Modulation of Collagen Arthritis by Rat Anti-Peptide 6 Monoclonal Antibody R34C Collagen arthritis was induced in DBA/1 mice. Mice were then treated with either rat anti-peptide 6 monoclonal antibody R34C or PBS. Arthritis was evaluated by measuring feet diameter.

Figure 10:
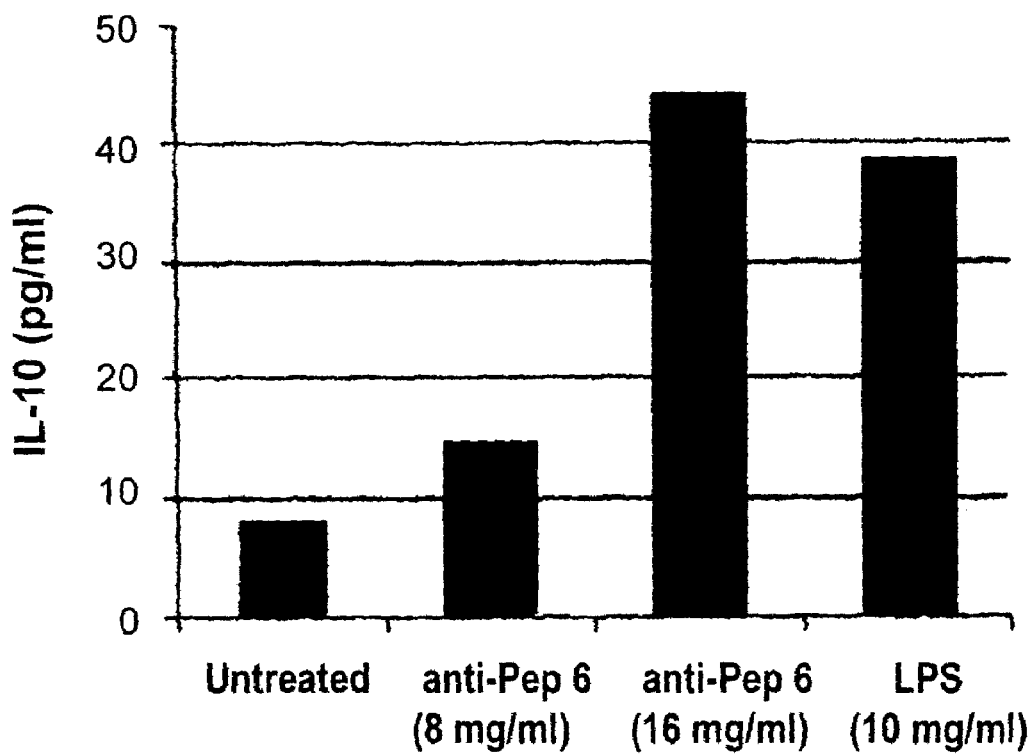

FIG. 10 Induction of IL-10 Secretion in Macrophages Incubated with Rat Anti-Peptide 6 R53F Monoclonal Antibody Naive human macrophages were incubated (24 h, 37° C., 5% $CO_2$) in RPMI with LPS (10 ng/ml) or with the rat monoclonal anti peptide 6 R53F antibody (8 and 16 μg/ml). Untreated cells served as control. IL-10 secretion to the medium was measured by ELISA.

Figure 11:
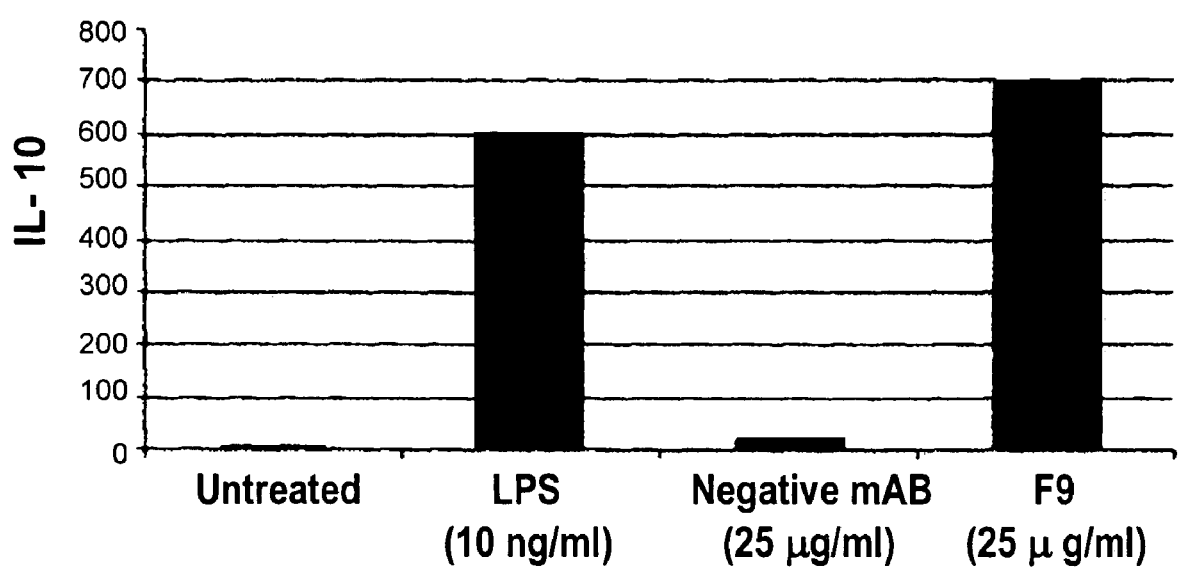

FIG. 11 Induction of IL-10 Secretion in Macrophages Incubated with Mouse Anti-Peptide 6 MF9 Monoclonal Antibody Naive human macrophages were incubated in RPMI with LPS (10 ng/ml), the mouse monoclonal anti peptide 6 MF9 antibody (25 μg/ml) or with mouse unrelated monoclonal antibody (25 μg/ml). Untreated cells served as control. IL-10 secretion (pg/ml) to the medium was measured by ELISA.

Figure 12A:
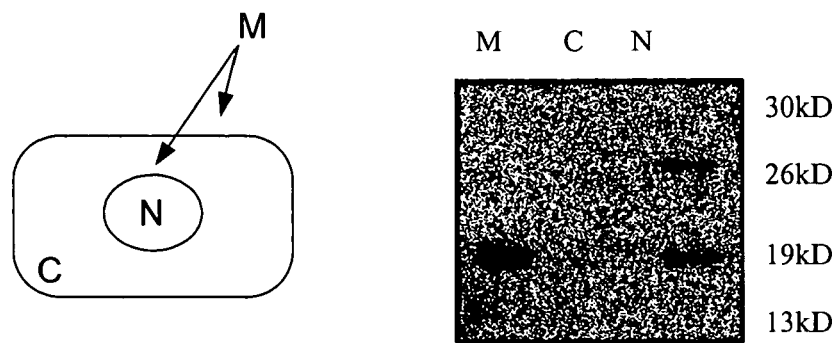

FIG. 12 Binding of Rat Anti-Peptide 6 Antibodies to Human Macrophages Cell Extract FIG. 12a: Human macrophages were fractionated to nuclear, cytoplasmic and membrane fractions. The fractions were resolved by SDS-PAGE and subjected to Western blotting using the monoclonal rat anti-peptide 6 R34C (10 μg/ml) antibody. The monoclonal antibody bound to 19 KD and 30 KD nuclear bands and to a 19 KD membrane band. Control polyclonal rat antibodies (10 μg/ml) did not bind to these bands (not shown).

Figure 12B:
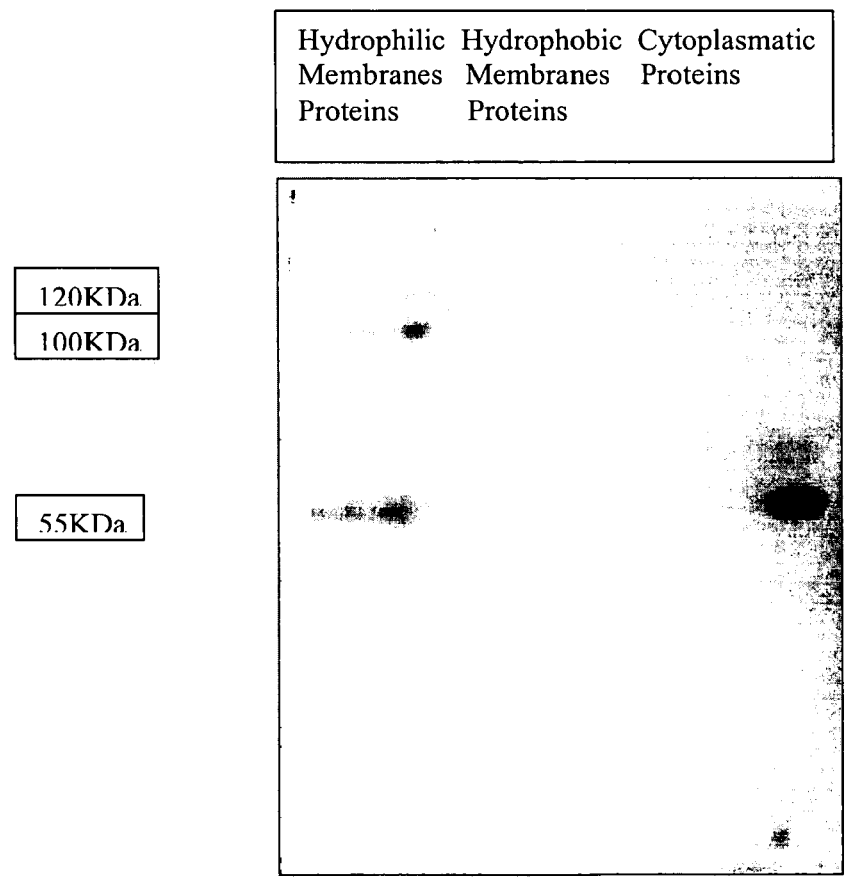

FIG. 12b: Human macrophages purified from human peripheral blood were fractionated to Hydrophilic membrane, Hydrophobic membrane and Cytoplasmic proteins. Ten micrograms (μg) of each macrophage protein fraction were resolved by 9% SDS-PAGE under denaturing conditions and subjected to Western blot analysis using 10 μg/ml rat monoclonal anti-peptide 6 antibody (clone B-24). B-24 monoclonal antibody showed a 120 KD, a 100 KD and a 55 KD bands in the Hydrophilic membrane fraction and a 55 KD band in the Cytoplasmic fraction. Control polyclonal rat antibodies (10 μg/ml) did not bind to these bands (not shown).

Figure 13:
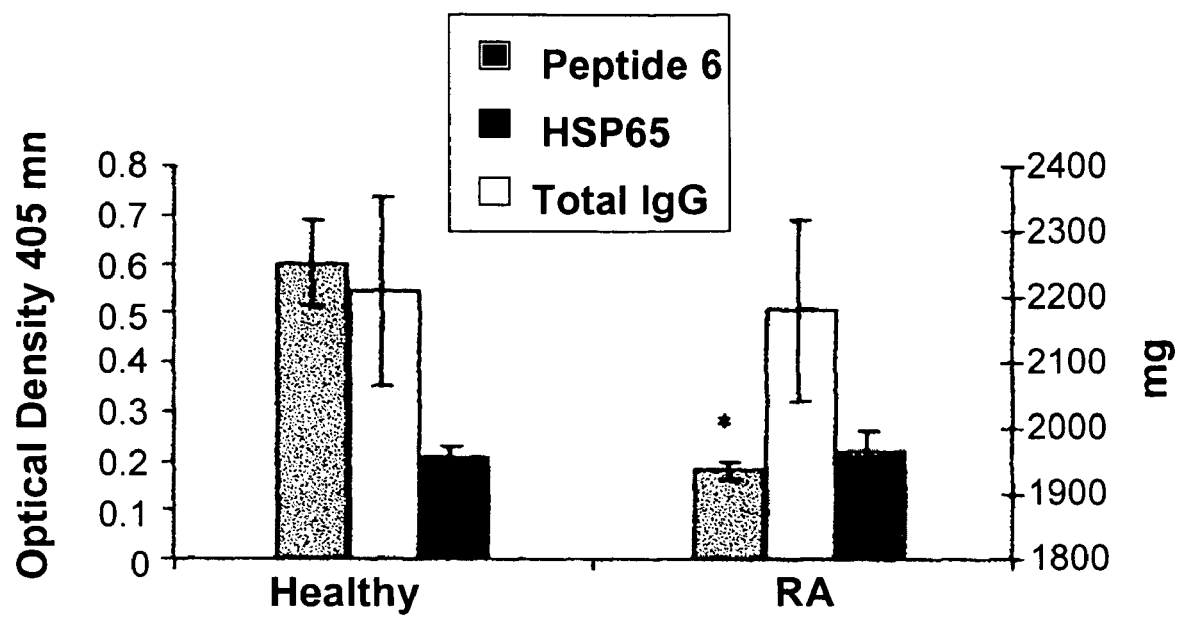

FIG. 13 Antibodies to Peptide 6 and to HSP 65 in RA Patients and Healthy Donors

Sera from healthy donors (n=17) or rheumatoid arthritis (RA) patients (n=25) were tested for antibody binding to peptide 6 and HSP 65 by ELISA and for immunoglobulin G levels. Anti-peptide 6 antibodies were found to be significantly lower in the RA patients (*p<0.01)

Figure 14:
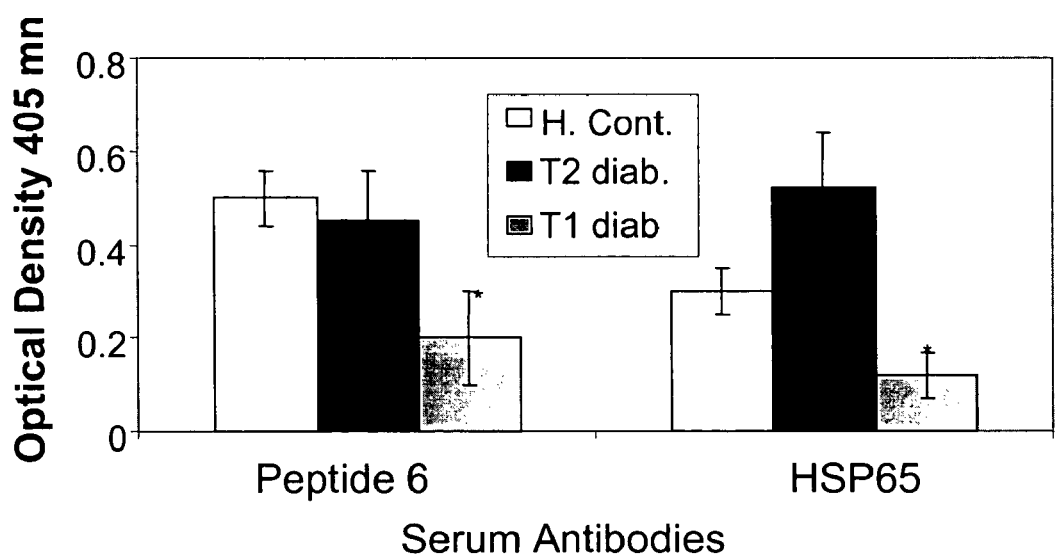

FIG. 14 Antibodies to Peptide 6 and to HSP 65 in Diabetic Patients and Healthy Donors Sera from healthy donors (n=11), type 1 diabetes patients (n=10) and type 2 diabetes patients (n=10) were tested for antibody binding to peptide 6 and HSP 65 by ELISA. Anti-peptide 6 antibodies were found to be significantly lower in type 1 diabetes patients (*p<0.05) compared to type 2 diabetes patients and healthy controls.

DETAILED DESCRIPTION OF THE INVENTION

The present invention relates to peptides comprising the amino acid sequence substantially as denoted by SEQ ID: No. 1, and biologically functional homologues and derivatives thereof.

Preferably, the peptide according to the first embodiment of the invention has the amino acid sequence substantially as denoted by SEQ ID: No. 2 or the amino acid sequence substantially as denoted by SEQ ID: No. 3.

The invention further relates to a peptide comprising the amino acid sequence substantially as denoted by SEQ ID: No. 4 and biologically functional homologues and derivatives thereof.

The invention also relates to a nucleic acid sequence which encodes a peptide according to the invention.

More particularly, the invention relates to a DNA sequence comprising the nucleic acid sequence substantially as denoted by SEQ ID: No. 5 and biologically functional derivatives thereof. This nucleic acid sequence encodes a peptide having the sequence substantially as denoted by SEQ ID: No. 4.

The invention further relates to vaccines comprising as active ingredient an effective vaccinating amount of at least one peptide of the invention, or a nucleic acid according to the invention. The vaccines of the invention are particularly useful in conferring immunity against autoimmune or inflammatory disorders.

Still further, the invention relates to antibodies directed against the peptides of the invention and to compositions comprising them. The compositions of the invention are particularly useful for the passive vaccination against autoimmune or inflammatory disorders. In addition, the invention also relates to new methods for diagnosis, prevention and treatment of inflammatory and autoimmune disorders.

The amino acid and nucleic acid sequences of the invention are presented in Table 1.

TABLE 1

| SEQ ID No | Peptide No. | Amino Acid or Nucleic Acid Sequence |
|---|---|---|
| 1 | | GPKGRNVVLEKKWGAPTITNDG |
| 2 | 6 | GPKGRNVVLEKKWGAP |
| 3 | 7 | VVLEKKWGAPTITNDG |
| 4 | R5 | TVIIEQSWGSPKVTKDGVTV |
| 5 | | GCCGCCATGGGACCAAAGGGACGCAACGTGG TACTAGAGAAGAAATGGGGCGCGCCGTAGCT CGAGA |

By the term "biologically functional homologues and derivatives" is meant any variations, including deletion, substitution and/or insertion of an amino acid residue in the amino acid sequences or a nucleic acid in the nucleic acid sequences of the invention which would not alter the biological activity of the peptides, or peptides encoded by the nucleic acid sequences, against autoimmune diseases. Thus, this term is to be taken to mean peptides with similar structure, peptides or their derivatives that are recognized by the protective antibodies and/or peptides or their derivatives that can induce protective antibodies upon immunization.

The invention further relates to DNA constructs comprising the nucleic acid sequence of the invention or functional homologues and derivatives thereof. The constructs of the invention may further comprise additional elements such as promoters, regulatory and control elements, translation, expression and other signals, operably linked to the nucleic acid sequence of the invention.

The invention also relates to a vaccine comprising as active ingredient an effective vaccinating amount of at least one peptide of the invention. The vaccines of the invention are particularly intended to confer immunity against inflammatory and autoimmune diseases, for example, rheumatoid arthritis or adjuvant arthritis.

By the term "effective vaccinating amount" is meant an amount sufficient to stimulate the immune system, directly or indirectly, and confer immunity against inflammatory and autoimmune diseases. Such effective amount is determined the severity of the disease, age, sex and weight of the patient, as well as the patient's general condition, and by other considerations known to the attending physician. Preferred doses, per injection, may be 0.02-2 mg/Kg body weight.

The vaccines of the present invention may alternatively comprise as the active ingredient at least one nucleic acid sequence according to the invention.

The vaccines according to the invention may optionally further comprise pharmaceutically acceptable carriers, diluents additives, excipients and adjuvants. By the terms "pharmaceutically acceptable carriers, diluents additives, excipients and adjuvants" is meant any inert, non-toxic material that may assist in the efficient delivery of the active ingredient.

The term "antibody" as used in connection with the present invention refers to both polyclonal and monoclonal antibodies. Polyclonal antibodies may be generated in rabbits, chicken, mice, rats, sheep, or similar mammals. The generation of polyclonal antibodies against peptides is described in the above-noted Current Protocols in Immunology, Wiley and Sons Inc. Chapter 9, fully incorporated herein by reference.

Monoclonal antibodies may be prepared from B cells taken from the spleen or lymph nodes of immunized animals, in particular rats or mice, by fusion with immortalized B cells under conditions which favor the growth of hybrid cells. For fusion of murine B cells, the cell line Ag-8 is preferred.

The technique of generating monoclonal antibodies is described in many articles and textbooks, such as the above-noted Chapter 2 of Current Protocols in Immunology. Chapter 9 therein describes the immunization of laboratory animals with peptides. Spleen or lymph node cells of these animals may be used in the same way as spleen or lymph node cells of protein-immunized animals, for the generation of monoclonal antibodies as described in Chapter 2 therein.

The term "antibody" is also meant to include intact molecules, as well as fragments thereof, such as, for example, Fv, Fab and F(ab')2, which are capable of binding antigen. Fab and F(ab')2 fragments lack the Fc fragment of intact antibody, clear more rapidly from the circulation, and may have less non-specific tissue binding than an intact antibody. An Fv fragment of an antibody is the smallest unit of the antibody that retains the binding characteristics and specificity of the whole molecule. The Fv fragment is a non-covalently associated heterodimer of the variable domains of the antibody heavy chain and light chain.

A "therapeutic antibody" is a single clone of a specific antibody that is produced from a cell line, including hybridomas. Humanized and immortal fusion cell lines that effectively and efficiently fuse with a mortal antibody producing human lymphocytes (B cells), create human hybridoma cells (hu-hybridomas) which have the antibody producing characteristics of the human lymphocytes.

The therapeutic antibodies in the invention can be murine antibodies; chimeric antibodies (combine the specificity of the murine antibody with the efficient human immune system interaction of a human antibody); humanized antibodies (the minimum mouse part from a murine antibody is transplanted onto a human antibody); and fully human antibodies (antibodies derived from transgenic mice carrying human antibody genes or from human cells). TransChromo (TC) technology allows to generate a wide variety of fully-human monoclonal antibodies using mice which carry the whole human immunoglobulin loci.

Human immunoglobulin phage display libraries are an additional source for isolation of human monoclonal antibodies to be used for therapeutic purposes.

An antibody is said to be "directed against" a molecule if it is capable of specifically reacting with the molecule to thereby bind the molecule to the antibody. The term "epitope" is meant to refer to that portion of any molecule capable of being bound by an antibody which can also be recognized by that antibody. Epitopes or "antigenic determinants" usually consist of chemically active surface groupings of molecules such as amino acids or sugar side chains and have specific three dimensional structural characteristics as well as specific charge characteristics.

An "antigen" is a molecule or a portion of a molecule capable of being bound by an antibody which is additionally capable of inducing an animal to produce antibody capable of binding to an epitope of that antigen. An antigen may have one or more than one epitope. The specific reaction referred to above is meant to indicate that the antigen will react, in a highly selective manner, with its corresponding antibody and not with the multitude of other antibodies which may be evoked by other antigens.

The antibodies of the invention may be provided in the form of compositions for use in passive immunization. While such compositions are generally administered by injection, it is not intended that the present invention be limited to this route alone. In general, however, the compositions of the invention are administered by intramuscular or subcutaneous injection. Occasionally, the intravenous or intraperitoneal routes may also be used to administer the compositions of the invention.

In addition to the active ingredient (i.e. the antibody), the compositions of the invention may also comprise a buffering agent, an agent which adjusts the osmolarity thereof, and optionally, one or more further additives, such as carriers, as known in the art.

A preferred buffering agent is phosphate-buffered saline solution (PBS), which solution is also adjusted for osmolarity.

A preferred composition is one lacking a carrier. Such formulations are preferably used for administration by injection, including intramuscular and intravenous injection.

The preparation of pharmaceutical and immunizing compositions is well known in the art and has been described in many articles and textbooks, see e.g., Remington's Pharmaceutical Sciences, Gennaro A. R. ed., Mack Publishing Company, Easton, Pa., 1990.

The amount of the therapeutic or pharmaceutical composition of the invention which is effective in the treatment of a particular disease, condition or disorder will depend on the nature of the disease, condition or disorder and can be determined by standard clinical techniques. In addition, in vitro assays as well as in vivo experiments may optionally be employed to help identify optimal dosage ranges. The precise dose to be employed in the formulation will also depend on the route of administration, and the seriousness of the disease, condition or disorder, and should be decided according to the judgment of the practitioner and each patient's circumstances. Effective doses may be extrapolated from dose-response curves derived from in vitro or animal model test systems.

For administration by injection, the formulations may be presented in unit dosage form, e.g. in ampoules or in multi-dose containers with an added preservative.

The compositions of the invention can also be delivered in a vesicle, for example, in liposomes. In another embodiment, the compositions can be delivered in a controlled release system.

As used herein, in the specification and in the claims section below, the term "treat" or treating and their derivatives includes substantially inhibiting, slowing or reversing the progression of a condition, substantially ameliorating clinical symptoms of a condition or substantially preventing the appearance of clinical symptoms of a condition.

Therefore, in a further embodiment, the compositions of the invention may be useful for treatment of or amelioration of inflammatory symptoms in any disease, condition or disorder where immune and/or inflammation suppression is beneficial such as, but not limited to, Rheumatoid arthritis and diabetes.

It has been shown that the development of autoimmune diabetes in the NOD mouse is marked by the presence of T-cells reactive to the p277 peptide of the HSP 60. It has further been shown that the p277 peptide can be used as a therapeutic vaccine to arrest NOD diabetes [28]. The p277 peptide has been shown to arrest also autoimmune diabetes induced by the Streptozotocin toxin [29]. Likewise, the vaccines according to the invention may also be used to suppress an autoimmune disease.

Furthermore, the vaccines of the invention may also be used to prevent relapses of autoimmune diseases, which characterize many autoimmune diseases. Prevention of a relapse is therefore part of the therapeutic approach to these disorders. The above peptide p277 has been shown to prevent NOD mice diabetes by turning off the anti-p277 immunity early in life. It was later shown to arrest autoimmune process even after it is far advanced [28].

Another possibility is that antibodies against the HSP molecule suppress inflammation by inhibiting the proinflammatory effect of the HSP on the innate immune system. Mycobacterial HSP 65 has been shown to induce release of pro-inflammatory cytokines from human monocytic cells [18] and the mammalian HSP 60 has been shown to synergize with IFN-γ and to promote pro-inflammatory cytokines like IL-12 and IL-15 [31]. Induction of anti-Mycobacterial/anti-self HSP antibodies may suppress those proinflammatory effects.

Specific immunoglobulins (antibodies) are commonly used for prevention and treatment of infectious diseases (i.e. viral hepatitis). This is termed passive vaccination. Immunoglobulins can also be used to suppress or prevent relapses of autoimmune diseases like ITP (Immune Thrombocytopenic Purpura), Myasthenia Gravis (MG), and other autoimmune diseases [30].

Thus, in yet a further aspect, the invention relates to an antibody directed against at least one peptide according to the invention or functional homologues and derivatives thereof, which can induce the production of said antibody.

The antibodies of the invention may be polyclonal or monoclonal antibodies.

In yet a further aspect, the invention relates to a composition for the passive immunization comprising at least one antibody according to the invention, and may optionally further comprise pharmaceutically acceptable carriers, diluents, additives, excipients and adjuvants. The composition of the present invention is particularly intended for the passive vaccination or immunization against, and treatment of autoimmune or inflammatory disorders, for example, rheumatoid arthritis.

By the term "therapeutic or immunological effective amount" is meant an amount sufficient to stimulate directly or indirectly immunity against inflammatory and autoimmune diseases. Such effective amount is determined the severity of the disease, age, sex and weight of the patient, as well as the patient's general condition, and by other considerations known to the attending physician. Preferred doses, per injection, may be 0.1-20 mg/Kg body weight.

The vaccines according to the invention may optionally further comprise pharmaceutically acceptable carriers, diluents additives and excipients.

The term "monitoring" used in connection with the present invention relates to a close ongoing medical surveillance complemented with periodical medical tests, to asses the disease course and severity.

The term "diagnosis" refers to the act of recognizing the presence of a disease from its signs or symptoms. In the present invention, diagnosis for Rheumatoid arthritis can be performed based on the results obtained using any immunological assays (calorimetric, fluorescent, magnetic, chemoluminescent or radioactive) capable of measuring antibodies amount, such as ELISA.

By the term "prognosis" used in the present application is meant predicting the course and termination of a disease.

The following Examples show the anti-MT HSP antibody response of various rats and its correlation with susceptibility to induction of arthritis. Only a limited number of epitopes in the bacterial HSP molecule is recognized by rat antibodies. The repertoire of this antibody differs between resistant and susceptible strains. Resistant strains were found to respond to peptides that are found on the outer surface of the molecule, as well as to the whole molecule. On the other hand, antibodies from naive Lewis rats reacted with a smaller number of peptides, which are less exposed on the outer surface of the molecule and did not react with the intact HSP. The presence of antibodies against some of the epitopes, as well as the whole MT-HSP, may be associated with resistance to the induction of arthritis and they were therefore named "protective" epitopes.

It has been previously reported that the T cell response to bacterial HSP shows determinant spreading. The present data, given in the following Examples, show that there is a clear B cell determinant spreading as well, and this spreading can occur also spontaneously, namely without intentional vaccination. The B cell epitopes, as will be shown, are different from the T cell epitopes. This observation is of particular significance to the present invention.

Young naive Lewis rats recognized only two bacterial epitopes; peptides 40 and 63. Four months Lewis rats recognized, in addition, peptides 6, 36 and 45 and nine months Lewis rats recognized peptides 7 and 31, in addition to all the other mentioned peptides. Recognition of these peptides is also associated with recognition of the whole bacterial HSP molecule.

The B cell epitope repertoire of the young BN rats is similar to that of the old Lewis rats including only one additional peptide, peptide 59. Lewis rats that were immunized with the CFA responded to all the aforementioned peptides, as well as to two additional peptides, namely 21 and 84.

Although all the anti HSP peptide antibodies found in naive old Lewis rats and in naive young BN rats are referred to as natural antibodies, it is possible that they are elicited as a response to the exposure of these rats to environmental pathogens (as "natural" antibodies may indeed always be) and that the epitope spreading in response to these pathogens occurs in the BN rat more rapidly, earlier and in more strongly than in the Lewis rat. Lewis rats have to be immunized with CFA in order to mimic the natural response of the BN rats. The similarity of the antibody repertoire of the naive BN rats to that of the immunized Lewis rat supports this possibility.

The nature of the B cell epitopes and the correlation between recognition of certain epitopes and the whole molecule can be better understood from primary and tertiary structure analysis of the molecule, shown hereafter.

To see whether the anti-HSP protective antibodies can be induced by immunization with the "protective" peptides, Lewis rats were immunized with the various peptides, without Freund's Adjuvant. Immunization with three peptides, the bacterial peptides 6 and 7, and the mammalian peptide 5, led to production of antibodies against bacterial peptide 6, as well as to an anti-HSP response, showing that antibodies against an "external" peptide will lead to recognition of the whole molecule. Induction of these antibodies also led to disease resistance.

Although the mechanism of disease resistance induced by the natural as well as the induced anti-HSP antibodies has not been yet clarified, it is possible that the antibodies against the MT HSP inhibit the early steps of induction of pathogenic T cells to the peptide by intervening in the antigen processing or the T cell recognition of the pathogenic epitopes. Alternatively they may prevent the effector steps of the pathogenic response by binding to the self HSP-cross reacting target antigen.

The T cell response of AA susceptible Lewis and AA resistant WKA Wistar rats to the bacterial HSP 65 KD has been thoroughly studied. It has been shown that in the early post immunization stages the Lewis T cells respond to several determinants found in the N terminal, as well as in the carboxy terminal of the molecule, whereas later a shift to carboxy terminal epitopes has developed. The early T cell response of Wistar rats was similar to that of the late response of the Lewis rats. As the 3D structure of the molecule does not show the carboxy and the N terminal sites to be in different locations of the molecule, it is not surprising that the B-cell epitopes were found all along the molecule without any selection of either the carboxy or the N terminal of the molecule.

A comparison between the published dominant T cell epitopes and the present B cell epitopes did not reveal common epitopes. To the contrary, the lack of natural antibodies to certain epitopes like 6, 7 or 31 in the naive Lewis rat is associated with an early T cell response to these epitopes, whereas the presence of antibodies to epitopes like 40 and 63 is associated with lack of an early T cell response. Based on these correlations, it may be suggested that the presence of natural antibodies to certain epitopes may actually inhibit T cell response to them, whereas the lack of antibodies enables the T cells to respond to these epitopes. For example, AA susceptible Lewis rats that do not have natural antibodies to the bacterial peptide 31 can develop a T cell response to this peptide, and these pathogenic T cells can induce arthritis.

As previously mentioned, there was a clear correlation between disease resistance and the presence of anti-HSP antibodies. Young naive Lewis rats did not have detectable antibodies against the HSP molecule whereas nine months old Lewis rats developed these antibodies in a significant titer. Parallel to the development of the anti-HSP response, the old rats also became resistant to induction of arthritis. Young Lewis rats acquired both the antibodies and disease resistance after immunization with CFA and the naturally resistant BN rats had anti HSP antibodies spontaneously, without the need for immunization. It is possible therefore that these antibodies bind the bacterial HSP immediately after immunization and prevent it from becoming accessible to the cellular arm of the immune system.

As noted previously, the epitopes "chosen" by the B cells from the bacterial HSP are epitopes that have relatively little homology with the self HSP, most probably as a result of tolerance to self antigens.

Analysis of the anti self (rat) HSP antibody repertoire indeed showed that there is a limited number of epitopes recognized by the rat immunoglobulins in the self HSP molecule. Naive young Lewis rats did not respond to any self peptide neither did they respond to the whole self HSP 60 molecule. BN and post-AA Lewis rats that reacted with 8-10 bacterial HSP epitopes responded to only two epitopes in the self HSP, peptides M5 and M30, as well as to the whole self HSP molecule.

Expression of the mammalian (or self) HSP is upregulated in inflamed synovia of rats with AA [22] and cross-reactive immune recognition has been found between the Mycobacterial HSP 65 KD and endogenous self HSP 60 KD at the T-cell level [23-25].

As the anti self antibodies were found only in the resistant rats, it is possible that antibodies that cross react with the self HSP may conceal it from the pathogenic T cells and thus act as protective antibodies.

It is interesting to note that one of the two self protective epitopes is the self peptide 5, which is the homologous rat epitope to the bacterial protective peptide 6. Moreover, immunization with the bacterial peptides 6 and 7 and with the mammalian peptide 5 led to the production of anti bacterial HSP 6 and anti bacterial HSP antibodies, as well as protection against disease induction. Observing the primary structure of these three peptides leads to the conclusion that they express a common motif (V-E-W G-P) which might be the protective motif of these peptides (FIG. 5).

Therefore, the humoral immune response to the bacterial HSP may be aimed at a limited number of potential B-cell epitopes. These epitopes are peptide stretches located between amino acids that serve as bends and spacers, and are found in non-conserved parts of the molecule. Recognition of B-cell epitopes that are exposed on the surface of the molecule leads to binding to the whole molecule and is associated with resistance to induction of arthritis.

This resistance occurs naturally in some strains of rats whereas in others it can be acquired with age or upon immunization with HSP. Immunization with some of the "protecting" epitopes can lead both to disease resistance as well as to the serological profile that is present in the resistant strains.

The present invention can also provide a method for the prediction of susceptibility/predisposition to develop autoimmune arthritis. In the rat system, it has been shown that naive young Lewis rats do not have antibodies against peptide 6 of the HSP and that they are susceptible to the development of arthritis after exposure to or immunization by HSP. In a similar manner, healthy individuals that lack sub-groups of antibodies against HSP specific peptides may be susceptible to onset of arthritis.

"Naturally" occurring anti-peptide 6 and anti-HSP antibodies are found in serum samples of normal controls and RA patient Although total immunoglobulin G amounts as well as anti-HSP antibody level are similar in both groups, anti-peptide 6 antibodies were found to be significantly lower (by 3 fold) in RA patients.

The present invention also provides an assay for the assessment and determination of susceptibility/predisposition to arthritis. The assay can be performed by ELISA, in which the peptides are bound to the solid phase and serum samples added, followed by adding anti human immunoglobulins. Other known immunological analysis techniques can also be used.

This invention provides a method for monitoring the patients' disease development and the possibility to evaluate the prognosis. This information can be of major importance in the decision of patient treatment course and the doses of the medication to be used. Assessment of anti-peptide 6 in patients' serum can be performed by ELISA or any other sensitive immune assay capable to detect antibodies.

In the animal models for arthritis, high level of anti-peptide 6 antibodies in rats prevented the induction of AA. The presence of anti-peptide 6 antibodies confers "protection" from arthritis and therefore passive vaccines based in humanized and human monoclonal anti-peptide 6 antibodies, as well as active vaccines using the peptide itself, should be considered as a new therapeutic approach for Rheumatoid arthritis.

The present invention can provide a method for the treatment of inflammatory and autoimmune disease. Active and passive vaccination using peptide 6 (SEQ ID: No. 2) or anti-peptide 6 antibodies induce a specific immune response that upon restriction to the inflammatory sites, may provide a specific localized treatment for inflammatory and autoimmune diseases. This specific treatment, in contrast to commonly used generalized anti-inflammatory drugs, may allow the use of small therapeutic doses and to avoid the drugs' secondary effects.

Active immunization with the bacterial HSP peptide 6 (SEQ ID: No 2) is also beneficial in autoimmune disorders, for instance autoimmune diabetes. NOD mice immunized with the mycobacterial peptide 6 produced antibodies against the peptide 6 and the whole HSP 65. The protective effect of these immunoglobulins is reflected by the delayed appearance of the diabetic symptoms and the significantly lower number of sick mice in the vaccinated group.

Resistance to AA is due to the presence of natural as well as acquired anti-heat shock protein (HSP) antibodies. Acquisition of these antibodies can be achieve by active or passive vaccination.

Active vaccination with peptide 6 induced anti-peptide 6 antibodies and suppressed the severity of AA. Lewis rats treated for AA induction and concomitantly with an anti-peptide 6 monoclonal antibody (R53F) showed up to 65% reduction in arthritis.

Similarly, treatment of DBA/1 mice, induced to develop Collagen arthritis (another animal model for arthritis), with an anti-peptide 6 monoclonal antibody (R34C) reduced arthritis severity.

Active vaccination with peptide 6 as well as passive vaccination with monoclonal anti-peptide 6 antibodies suppress significantly AA in Lewis rats and collagen arthritis in mice, proving evidence for the efficacy of the treatment.

Treatment of arthritis susceptible animals with anti-peptide 6 antibodies leads to the suppression of arthritis. Passive vaccination with human monoclonal anti-peptide 6 antibodies provides a new therapeutic tool for selective anti-inflammatory suppression of human arthritis.

The anti-inflammatory effect of these antibodies is obtained by the induction of the anti-inflammatory IL-10 cytokine. Exposure of macrophages to anti-peptide 6 antibodies elicits sequential events resulting eventually in the up-regulation of the IL-10 gene expression. The increase of IL-10 secretion in the inflammatory site can divert the local cytokine profile from an inflammatory to an anti-inflammatory response and thus explain the mechanism of protection against inflammation rendered by these antibodies.

Induction of IL-10 secretion is a direct effect of the interaction of the antibodies with macrophage proteins and does not require the presence of any HSP antigen. The anti-peptide 6 monoclonal antibodies bind specifically to human macrophage membrane proteins, as further described in page 23 and illustrated in FIGS. 12a and 12b.

The present method for the treatment of inflammatory and autoimmune disease can be provided by injection (e.g. sub dermal or intramuscular) or by any conventional approach to deliver active peptides or antibodies.

The invention will be described in more detail on basis of the following Examples, which are illustrative only and do not in any way limit the invention. Many modifications and variations of the present invention are possible in light of the present teachings. It is therefore understood, that within the scope of the appended claims, the invention may be practiced otherwise than specifically described.

EXAMPLES

Materials

Animals: Female inbred Lewis rats, 6 weeks or 9 months old, were obtained from Harlan Lab. Israel. Female Brown-Norway (BN) rats, 6 weeks old, were obtained from Harlan Sprague-Dawley, USA.

Antigens and antibodies: Recombinant HS P65 of *Mycobacterium Tuberculosis* was a gift from Dr. M. Singh (The WHO Recombinant Protein Bank, Germany). Recombinant mammalian HSP 60 was purchased from StressGen Biothec. Corp. (Victoria, BC, Canada). Synthetic peptides of MT HSP 65 were a gift from Dr. L. Adorini (The Roche Milano Ricerche, Milano, Italy). Synthetic peptides 6 and 7 of MT HSP 65 and R5 of mammalian HSP 60, (SEQ ID: Nos. 2, 3 and 4 respectively) were synthesized by standard solid phase 9-FMOC technology. The peptides were purified by reverse phase HPLC and analyzed by Fast Atom Bombardment Mass spectrometry at the Weizmann Institute, Rehovot, Israel.

Synthetic peptides of the mammalian HSP 60 were a gift from Dr. I. Cohen (The Weizmann Institute, Rehovot, Israel).

Goat anti Rat IgG conjugated to alkaline-phosphatase was purchased from Jackson ImmunoResearch Lab. Inc. (Avonsdale, Pa.).

Methods

Induction and Clinical Assessment of Adjuvant Arthritis: Lewis rats were injected with 1 mg of Mycobacterium Tuberculosis H37Ra (Difco, Detroit, Mich.) in Complete Freund's Adjuvant (Difco) subcutaneously at the base of the tail. Severity of Arthritis (arthritis index) was assessed blindly as follows: 0—no arthritis; 1—redness of the joint; 2—redness and swelling of the joint. The ankle and tarsal-metatarsal joints of each paw were scored. A maximum score of 16 can be obtained, but a score above 8 indicates a severe disease.

Dot Blots assay: Antigens were dissolved in PBS and samples of 1 µg were adsorbed on Nitrocellulose paper. The paper was air-dried and incubated with BSA 1% in PBS for 20 min. to block non-specific binding. The samples were then washed in PBS-Tween 0.05% and incubated with rat sera diluted 1:100 in BSA-PBS, for 90 min. at room temp. Samples were washed and incubated with goat anti rat antibody conjugated to alkaline phosphatase diluted 1:1000 in BSA-PBS for 90 min. at RT. After re-washing the color reaction was developed by adding a mixture of BCIP-NBT (Sigma-Fast, Sigma) to the cells for 15 min. The reaction was stopped by the addition of tap water.

ELISA: Flat-bottomed 96 well plates (Corning) were coated with mammalian HSP 60 or Mycobacterial HSP 65 (10 µg/ml) in carbonate buffer pH 9.6 overnight at 4° C.

After extensive washing with PBS-Tween 0.05% plates were incubated with blocking buffer containing 1% BSA (Sigma) for 60 min. at RT.

HSP peptides were attached to plates pre-treated with glutaraldehyde according to Kasprzyk et al. [26]. Shortly, plates were coated with 100 µl/well of 5% w/v of glutaraldehyde in PBS for 1 hour at room temp. Plates were washed thoroughly with PBS and peptides (1 µg/100 µl) were added to each well, incubated overnight at 4° C. Plates were shaken dry and blocked with BSA 1% in PBS.

Plates coated with either HSP or peptides were washed again and incubated with rat sera diluted 1:100 with PBS-Tween 0.01% for 90 min. at room temp. After re-washing the plates were incubated with Goat anti rat IgG or IgM conjugated to alkaline-phosphatase for 60 min. at room temp. The presence of antibodies was revealed by addition of the substrate PNP (NP 100, Chemicon, Temecula, Calif.) to the plates. Optical density was measured photometrically at 405 nm.

Preparation of human monoclonal anti-peptide 6 antibodies: Human monoclonal anti-peptide 6 antibodies are prepared by the following technique: blood samples are collected from healthy volunteers and they are tested for the presence of anti-peptide 6 antibodies (by a specific ELISA for peptide 6). B cells from positive individuals are transformed by EBV according to the method of Steinitz et al. [34]. Anti-peptide 6 positive clones are re-cloned and expanded.

Western blot analysis of human macrophages proteins fractions using anti-peptide 6 Monoclonal Antibodies Human macrophages are purified from human peripheral blood. The WBC are separated from RBC by Ficoll and incubated in RPMI medium containing 2% human serum at 37° C. for 9 minutes. After the incubation, non-adherent lymphocytes cells are washed away with PBS, leaving only adherent macrophages cells in the tissue culture plate.

Hydrophilic Membrane, Hydrophobic Membrane and Cytoplasmic proteins, are purified from the human macrophages cell using ReadyPrep™ Protein Extraction kit (Membrane I) and ReadyPrep™ Protein Extraction kit (Cytoplasmic) (Bio-Rad Laboratories, Inc., Hercules, Calif. 94547, USA).

Ten micrograms (10 µg) of each macrophage protein fractions are boiled in sample buffer containing SDS and β-mercaptoethanol and resolved at 9% SDS-PAGE The separated proteins are transferred to nitrocellulose by the Western blot technique and incubated with supernatant from a rat anti-peptide 6 antibody secreting hybridoma (clone B-24). Total rat IgG (10 µg/ml) are used as negative control. The binding intensity was detected by Goat anti-rat IgG and IgM Fc Peroxidase conjugated (HRP) (Jackson Immunoresearch Laboratories, Inc., West Grove, Pa. 19390, USA) were used as secondary antibodies and the signal was developed using a chemiluminescence detection system.

Amino Acid Comparison: "Pileup" and "pretty" programs (GCG—Wisconsin package, v.9.0) were used to compare amino acid sequences of three HSP 60 (Mycobacterium Tuberculosis, rat and human).

Structure Analysis: RasMol v. 2.6 program and the 3D structure of the *E. coli* complex GroEL-GroES (pdb ID: 1AON reference) were used to analyze the position of epitopes.

Since the crystal structure of MT HSP 65 KD is not yet completely known, a three-dimensional model for the tertiary structure of MT HSP 65 KD based on the solved crystal structure of GroEL from *E. coli* (pdb ID: 1GRL) was used as template. This model was built by programs for comparative protein modeling.

Modulation of AA by mycobacterial and mammalian HSP peltides: HSP 65 derived peptides were tested for their ability to modulate the appearance or severity of AA in Lewis rats. Rats were immunized with 100 µg of each peptide in PBS, three weeks (3W), 2W and 1W before induction of AA by MT. Control rats received PBS. Rats were bled for testing antibody presence before injection of MT and 30 days post MT injection.

DNA Vaccine preparation: A synthetic oligoDNA, having the SEQ ID: No. 5, encoding the oligopeptide Mycobacterium Tuberculosis HSP 65 KD No. 6, presented in Table 1, was cloned into the commercially available mammalian expression vector, pTARGET (Promega, Madison, Wis., USA), having the restriction map depicted in FIG. 6. The cloning was carried out according to the manufacturer's instructions.

The plasmid construct was then transferred into *E. coli* JM109 strain and expanded to large scale for further plasmid BN rats, and Lewis rats that were immunized with CFA reacted also with peptides 21 (residues 121-136) and 84 (residues 499-514). It is noted that although naive Lewis rats do not recognize the whole molecule of HSP 65 KD, its immunoglobulins can interact with certain peptides of this molecule, without any effect on susceptibility to AA.

TABLE 2

Antibodies to Mycobacterial HSP 65 Peptides

| | Peptide Sequence | | | | | | | | | | | |
|---|---|---|---|---|---|---|---|---|---|---|---|---|
| Strain | 21<br>121-136<br>SEQ ID<br>#10 | 84<br>499-514<br>SEQ ID<br>#17 | 59<br>349-364<br>SEQ ID<br>#15 | 7<br>37-52<br>SEQ ID<br>#3 | 31<br>181-196<br>SEQ ID<br>#11 | 6<br>31-46<br>SEQ ID<br>#2 | 36<br>211-226<br>SEQ ID<br>#12 | 45<br>265-280<br>SEQ ID<br>#14 | 40<br>236-251<br>SEQ ID<br>#13 | 63<br>373-388<br>SEQ ID<br>#16 | HSP<br>65 | Disease<br>Susceptibility |
| Lew-6w | − | − | − | − | − | − | − | − | + | + | − | 8/10 |
| Lew-4m | − | − | − | − | − | + | + | + | + | + | − | 3/5 |
| Lew-9m | − | − | − | + | ++ | + | + | + | ++ | +++ | + | 0/7 |
| BN-6w | − | − | + | + | + | + | ++ | + | ++ | + | +++ | 0/10 |
| Lew-Post AA | + | + | +++ | + | ++ | +++ | +++ | ++ | ++ | ++ | ++ | 0/10 |

O.D:
<O.15 = −;
0.16-0.45 = +;
0.46-0.75 = ++;
>0.75 = +++ purification, using the DNA purification system Wizard Plus Maxipreps kit (Programa, Madison, Wis., USA).

Animal vaccination: Lewis rats were pre-treated with Bupivaccine (Astra) two days prior to vaccination and later disease induction. The rats were then twice injected with 100 μg of the DNA construct, into the tibialis anterior muscle, with a week interval between the injections.

Results

The Interaction of Rat Immunoglobulins with whole Mycobacterial HSP 65 and its Peptides Previous experiments conducted by the inventors showed that immunoglobulins from AA resistant naive rats (i.e. BN or Fisher) as well as Lewis rats that recovered from AA (post AA Lewis rats), were able to suppress the induction of AA in naive Lewis rats and bound to the bacterial HSP 65 in a dot blot assay. To obtain a more quantitative evaluation of this binding, the interaction of immunoglobulins from these rats with the whole molecule of the Mycobacterial HSP 65, known to be associated with AA in Lewis rats, was tested by Dot-Blot and ELISA.

It was found that immunoglobulins from 6-8 week old BN rats, and post AA Lewis rats, reacted strongly with the HSP while no reaction was found when immunoglobulins from naive Lewis rats were tested. Interestingly, it was found that immunoglobulins from nine months old naive Lewis rat also reacted with the HSP.

To define the epitopes recognized by the anti bacterial HSP antibodies, the inventors tested by Dot-Blot the interaction of immunoglobulins from naive young BN rats and post AA Lewis rats with 90 16-mer synthetic peptides of the Mycobacterial 65 KD HSP. Immunoglobulins from naive young Lewis rats served as control.

Only 10 peptides out of the 90 peptides tested (Table 2) reacted with the immunoglobulins tested. All of the rats immunoglobulins reacted with two peptides: 40 (residues 235-250) and 63 (residues 373-388). When these rats age, they acquire antibodies against additional peptides, and a similar profile to that of old Lewis rats is found in young naive Binding of Rat Immunoglobulins with the Mammalian HSP 60 and its Peptides Previous studies have shown that certain bacterial HSP peptides may trigger self HSP reactive T-cells with disease suppressive regulatory potential. To analyze the anti self-HSP antibody repertoire of these rats, the reactivity of Ig's from naive and post AA Lewis rats as well as from naive BN rats to whole mammalian HSP 60 was tested by ELISA.

The results presented in Table 3 indicate that that naive and four months old Lewis rats do not possess anti self-HSP 60 antibodies, whereas nine months old Lewis rats, young BN rats and post-AA Lewis rats had significant binding to the self-HSP (Table 3). Some naive Lewis rats had very low concentrations of the antibodies.

TABLE 3

Antibodies to Mammalian HSP 60 Peptides

| | Peptide Sequence | | | Disease |
|---|---|---|---|---|
| Strain | M 5 61-80 | M 30 436-455 | M-HSP 60 | Susceptibility |
| Lew-6w | − | − | − | 8/10 |
| Lew-4m | − | − | − | 3/3 |
| Lew-9m | ++ | ++ | + | 0/7 |
| BN-6w | + | + | + | 0/10 |
| Lew-Post AA | +++ | ++ | + | 0/10 |

O.D.: <O.15 = −;
0.16-0.45 = +;
0.46-0.75 = ++;
>0.75 = +++

Immunoglobulins from naive Lewis and BN rats and post-AA Lewis rats were tested for binding to 38 synthetic 20-mer peptides of the mammalian HSP 60 by Dot-Blot. It was found that immunoglobulins derived from BN and post-AA Lewis rats, but not from naive Lewis rats, reacted with 2 peptides only: peptide 5 (residues 61-80) and peptide 30 (residues 436-455). Quantitative analysis of this binding as well as the binding of immunoglobulins from four and nine month old Lewis rats confirmed the dot blot findings (Table 3).

Amino Acid Comparison

The HSP 60 family is highly conserved: MT-HSP 65 and its mammalian homologues (rat or human) show 48% identity. In FIG. 1, the three amino acid sequences of the MT-HSP 65, HSP 60 from rat and human are compared. The consensus sequence of these three proteins is shown too. The epitopes that were found to be relevant in this study are shown in Bold and Underlined.

3D Structure Analysis

Tertiary structure plays an important role for B-cell epitope recognition. In a first approach, a simple computer program was provided, that could predict where to find potential B-cell epitopes by screening the primary structure of the peptide. The algorithm is based on a previous analysis by Warren et al. [27] of the Myelin Basic Protein to locate potential epitopes for B-cell. According to their analysis, two sorts of amino acids can be defined:

"Molecular spacers": These are short-chain residues (side chains of one carbon or less) that could provide a molecular gap for adjacent long-chain amino acids. Three amino acids that fit this definition are: Glycine (G), Alanine (A) and Serine (S).

"Molecular bends": Proline (P) residues that can cause disruptions in secondary structure.

A minimal length of 9 residues for these potential epitopes was set. Following these rules, six series of consecutive long-chain residues (side chains of two carbons or more) located between molecular spacers and/or molecular bends were found (Table 4).

In order to better understand the implications of the tertiary structure of MT HSP 65 KD and to locate these different amino acid sequences on the whole molecule, a model for the tertiary structure of MT HSP 65 KD based on the crystal structure of *E. coli* GroEL (FIG. 3) was used.

Structure analysis confirmed that the experimentally recognized epitopes located on the surface of the protein can provide a potential site to antibodies binding. Peptides 6, 7, 21, 31, 59 were those that were found to be the most exposed whereas peptides 36, 40, 45, 63 and 84 are partially exposed.

The single potential epitope that was not recognized experimentally (residues 318-331) seems to be "buried" in the molecule.

Although there is a marked homology between MT HSP 65 KD and mammalian HSP 60 KD, most of the peptides that were found to be recognized by the anti-MT HSP 65 antibodies did not show high residues homology with the mammalian HSP. This may be due to the tolerance to self that protects the rats from developing an autoimmune autoantibody response to their own HSP 60. Two peptides, 6 and 45, did not seem to conform to this rule as they had sites showing high homology to the self HSP.

These findings may be explained for both peptides as follows:

As to peptide 6 (residues 31-46): antibodies were found to bind peptide 7 (residues 37-52) which overlap the polymorphic part of this peptide, and the mammalian peptide 5 (residues 61-80) representing the region homologous with the mammalian HSP. It seems, that these antibodies are directed against the polymorphic (non-self) region of peptide 6 (residues 40-46). It can also provide a hypothesis concerning the

TABLE 4

Potential epitopes of MT HSP 65 KD

| Location of the peptide (aa residues) | Sequence of the peptide | Length | SEQ ID No. | Experimental peptide matching |
|---|---|---|---|---|
| 35-43 | G-RNVVLEKKW-G | 9 | 18 | 6,7 |
| 123-132 | A-VEKVTETLLK-G | 10 | 19 | 21 |
| 135-143 | A-KEVETKEQI-A | 9 | 20 | 21 |
| 319-332 | RKVVVTKDAETTIVE | 14 | 21 | none |
| 357-367 | S-DYDREKLQERL-A | 11 | 22 | 59 |
| 383-396 | A-TEVELKERKHRIED-A | 14 | 23 | 63 |
| 183-195 | G-LQLELTEGMRFDK-G | 13 | 24 | 31 |
| 259-270 | S-TLVVNKIRGTFK-S | 12 | 25 | 45 |

Five of six series that were identified by these rules fit amino acid sequences that were found to be experimentally recognized by B-cell antibodies (Table 4). Consequently, in order to find more epitopes, the program was run with a slight change, namely search of epitopes that contain at most one molecular spacer (G, S or A). The minimal length was set at 12 residues (instead of 9 previously) in order to lower the background (i.e., a penalty of three residues was set to compensate the gap). Two new sequences were identified, that were also found to be experimentally recognized by B-cell antibodies (peptides 31, 45; see Table 4). The molecular spacer was glycine in these two cases.

"protective" ability of this peptide, partial homology to the mammalian HSP 60 sequence may be responsible for this protective effect.

As to peptide 45 (residues 265-280): This peptide can be divided into two consecutive regions: one polymorphic (residues 265-271) and the second highly conserved (residues 271-280). Analysis of the three-dimensional structure shows that the polymorphic region is the exposed region, whereas the conserved region seems to be "buried" in the whole molecule (not shown). Therefore, it is possible that the antibodies that bind peptide 45 are mainly directed against the exposed polymorphic region.

No particularity concerning the secondary structure and the repartition of hydrophobic/polar residues in these epitopes was noticed (both experimentally and computer recognized). Generally, the experimentally recognized epitopes tend to be hydrophobic (9-12 hydrophobic residues out of 16), but for peptide 59 that is highly polar (13 residues out of 16).

With reference to the Figures, FIG. 2 shows the location of bacterial peptides 6, 7 and 31 on the three dimensional structure of the *E. Coli* GroEL-GroES complex and FIG. 3, as stated, shows the same peptides on a model of the MT HSP 65 based on the structure of GroEL *E. Coli* with a space-filling and secondary structure representations.

Analysis of the Ability of Peptides to Immunize against AA

To test whether active immunization with bacterial or mammalian HSP peptides that are recognized by protective immunoglobulins can induce protection against AA, Lewis rats were immunized with the mycobacterial peptides 6, 7, 21, 31, 36, 45, 84, that bound antibodies from resistant Lewis rats ("protective" peptides), with some non-reactive mycobacterial HSP 65 peptides: peptide 26 (residues 151-166), 28 (residues 163-178) or peptide 70 (residues 415-430), and with the mammalian peptide 5.

Rats were injected 3 times intraperitoneally (IP), with one week intervals between injections before induction of AA with MT.

FIG. 4 shows that only pre-immunization of rats with the bacterial peptides 6 and 7 and the mammalian peptide 5 resulted in a significant suppression of disease severity.

Immunization with these "protective" peptides also resulted in the production of antibodies against peptide 6 as well as against the whole MT HSP 65 (Table 5).

TABLE 5

Anti HSP Antibodies in Immunized Lewis Rats

| Immunizing Peptide | Antigen | | | |
|---|---|---|---|---|
| | 6 | 7 | M5 | MT-HSP 65 |
| PBS | − | − | − | − |
| 6 | ++ | − | − | ++ |
| 7 | + | − | − | + |
| M5 | + | − | − | + |

O.D.:
<O.15 = −;
0.16-0.45 = +;
0.46-0.75 = ++;
>0.75 = +++

Analysis of the Ability of Peptide 6 to Immunize against Autoimmune Diabetes

To test whether active immunization with the bacterial HSP peptide 6 (SEQ ID: No. 2) can induce protective immunoglobulins against other autoimmune disorders, for instance autoimmune diabetes, NOD mice were immunized with the mycobacterial peptide 6 ("protective" peptide). Naive NOD mice were immunized 3 times I.D. with either 100 µg peptide 6 in CFA and IFA or PBS (control). Mice were monitored for the onset of diabetes by glucose test (appearance of hyperglycemia) and for anti-peptide 6 or anti-HSP 60 antibodies by ELISA. Mice immunized with the peptide developed anti-peptide 6 as well as anti-HSP 65 antibodies as reflected by OD (1.52±0.07 and 1.43±0.13 respectively) in comparison to CFA immunized mice (0.05±0.01and 0.01±0.01) and control mice (0.09±0.06 and 0.16±0.16).

FIG. 7 shows that in NOD mice immunized with the bacterial peptide 6, the appearance of the diabetic symptoms was clearly delayed and the disease severity was significantly reduced.

Immunization with this "protective" peptide resulted in the production of antibodies against peptide 6 and against the whole HSP 65, which delayed the appearance of diabetes and significantly lowered the number of sick mice in the peptide-6 vaccinated group.

Level of Anti-Peptide 6 and Anti-HSP 65 Antibodies in Diabetic Patients and Healthy Donors The presence of anti-peptide 6 and anti-HSP antibodies in serum samples from normal and diabetic patients (type 1 and type 2) was evaluated. Sera from healthy donors (n=11), type 1 diabetes patients (n=10) and type 2 diabetes patients (n=10) were tested by ELISA for the presence of antibodies that bind to peptide 6 and HSP 65. Anti-peptide 6 antibodies were found to be significantly lower in type 1 diabetes patients (*p<0.05) compared to type 2 diabetes patients or healthy controls (as shown in FIG. 14). The difference between diabetic patients and controls was specific for the type 1 and not for type 2 diabetes patients. Anti-peptide 6 antibodies level was similar in these two groups: type 2 diabetes patients and controls. Although anti-HSP antibody level varied among the groups, the lowest titer was observed in type 1 diabetes patients.

Immunization of NOD mice with the "protective" peptide results in the production of antibodies against peptide 6 and the whole HSP 65. Consequently an attenuation of the disease symptoms can be observed. Consistent with this idea, it was found that patients suffering from type 1 diabetes have low amounts of these antibodies. Therefore, evaluation of the anti-peptide 6 serum titer level may be useful for predicting the predisposition of an individual to develop autoimmune diabetes.

Treatment of Autoimmune Arthritis by Protective Antibodies against a Heat Shock Protein Surface Epitope Resistance to AA is due to the presence of natural as well as acquired anti- heat shock protein (HSP) antibodies. These antibodies are directed against peptide 6, a 16 amino-acid peptide from the bacterial HSP (residues 31-46).

As active vaccination with peptide 6 induced anti-peptide 6 antibodies and suppressed the severity of AA, the effect of a passive treatment with a rat anti-peptide 6 monoclonal antibody R53F was tested. Lewis rats were immunized with MT in CFA to induce AA and concomitantly treated with R53F a rat anti-peptide 6 monoclonal antibody, with an unrelated rat monoclonal antibody (R83D) or PBS (control). The antibodies were first administrated IV and IP the following day.

Treatment with R53F, a rat anti-peptide 6 monoclonal antibody, reduced arthritis severity by 65% on day 25 (FIG. 8). The rat control unrelated monoclonal antibody R83D, had no significant effect on the severity of AA. Active vaccination with peptide 6 as well as passive vaccination with monoclonal anti-peptide 6 antibodies suppressed significantly AA in Lewis rats.

Rat Monoclonal Anti-Peptide 6 Antibody Modulation Effect on Collagen Arthritis Severity (a Mouse Autoimmune Arthritis Model).

DBA/1 mice induced to develop Collagen arthritis were treated with either anti-peptide 6 monoclonal antibody R34C or PBS (control). Arthritis was evaluated by measuring feet diameter.

Treatment with R34C, a rat anti-peptide 6 monoclonal antibody, reduced arthritis severity (FIG. 9).

Active vaccination with peptide 6 as well as passive vaccination with anti-peptide 6 monoclonal antibody suppressed significantly murine collagen arthritis.

The Anti-Inflammatory Effect of Mouse, Rat and Human Anti-Peptide 6 Antibodies Mechanism.

To test whether the protective action of anti-peptide 6 antibodies is due to their influence on inflammatory cytokines, a series of experiments were performed. The effect of polyclonal and monoclonal anti-peptide 6 antibodies on cytokine secretion was analyzed in vitro.

In previous experiments [33], supernatant samples collected from human and naive Lewis rats PBMC incubated with LPS, with naive Lewis rat polyclonal IgG or with polyclonal anti-peptide 6 antibodies were tested for IL-10 secretion.

Anti-peptide 6 induced at least a six-fold higher secretion of IL-10 by rat PBMC compared with the control. The effect was specific to the anti-peptide 6 antibodies as IgG from naive Lewis rats did not show a similar effect. Incubation of murine and human mononuclear cells with the protective antibodies induced a significant increase in the secretion of IL-10. The use of a human monoclonal antibody induced 15 fold increase in the secretion of IL-10 by human macrophages. Induction of IL-10 was a direct effect of the interaction of the antibodies with the macrophages and did not require the presence of any HSP antigen.

Induction of IL-10 Secretion upon Incubation with Rat Anti-Peptide 6 R53F Monoclonal Antibody Naive human macrophages were incubated with LPS (10 ng/ml) or with the rat monoclonal anti-peptide 6 R53F antibody (8 and 16 μg/ml). Untreated cells served as control. IL-10 secretion to the medium was measured by ELISA. FIG. 10 shows that IL-10 secretion in the samples incubated with 16μg/ml R53F antibody was at least 4 times higher than in the control samples.

Induction of IL-10 Secretion upon Incubation with Mouse Anti-Peptide 6 MF9 Monoclonal Antibody Naive human macrophages were incubated with LPS (10 ng/ml), with the mouse monoclonal anti-peptide 6 MF9 antibody (25 μg/ml) or with a mouse unrelated monoclonal antibody (25 μg/ml). Untreated cells served as control. IL-10 secretion (pg/ml) to the medium was measured by ELISA.

As seen in FIG. 11, the presence of the mouse monoclonal anti-peptide 6 MF9 antibody induced 14-15 fold increase in the secretion of IL-10 by the human macrophages.

Binding of Rat Anti-Peptide 6 to Human Macrophages Cell Extract

In order to understand in what manner anti-peptide 6 antibodies induce IL-10 secretion, human macrophage were fractionated to nuclear, cytoplasmic and membrane fractions. The different fractions were resolved by SDS-PAGE and subjected to Western blotting using the monoclonal rat anti peptide 6 (10 μg/ml). The monoclonal antibody showed a 19 KD and 30 KD nuclear bands and a 19 KD band in the membrane fraction (FIG. 12a). Polyclonal rat antibodies (10 μg/ml) used as negative controls, did not bind to any of these bands.

The R34C anti-peptide 6 monoclonal antibodies bound specifically to a 30 KD surface molecule on the human macrophages membrane.

Purified human macrophages were fractionated to hydrophilic membrane, hydrophobic membrane and cytoplasmic proteins, using a different fractionation method. The different fractions were separated in SDS-PAGE, transferred to nitrocellulose and incubated with a rat anti-peptide 6 hybridoma supernatant (clone B-24).

A 55 KD, 100 KD and 120 KD hydrophilic membrane proteins bands were recognized by this antibody. A 55 KD band was also recognized in the cytoplasmic fraction (FIG. 12b).

Level of Anti-Peptide 6 and Anti-HSP 65 Antibodies in Rheumatoid Arthritis (RA) Patients and Healthy Donors The presence of anti-peptide 6 and anti-HSP antibodies in normal and RA patient serum samples was evaluated. Sera from healthy donors (n=17) or RA patients (n=25) were tested for antibody binding to peptide 6 and HSP 65 by ELISA and for immunoglobulin G levels. Anti-peptide 6 antibodies were found to be significantly lower (by 3 fold) in the RA patients (*p<0.01) when compared to control samples (as shown in FIG. 13). This difference between RA patients and control was specifically for anti-peptide 6 antibodies, since total immunoglobulin G amounts, as well as anti-HSP antibody level, was similar in both groups.

These results are sustained by previously described experiments in animal models for arthritis, in which high level of anti-peptide 6 antibodies in rats prevented the induction of AA. The presence of anti-peptide 6 antibodies confers "protection" from arthritis and therefore passive vaccines based in humanized and human monoclonal anti-peptide 6 antibodies, as well as active vaccines using the peptide itself, should be considered as a new therapeutic approach for Rheumatoid arthritis.

REFERENCES

1. Pearson, C. M., Proc. Soc. Exp. Biol. Med. 91:95-101 (1956)
2. Pearson, C. M. & Wood, F. D., Arthritis Rheum. 2:440 (1959)
3. Waxman, B. H. and Wemersten, C., Int. Arch. Allergy 23:129 (1963)
4. Ulmansky, R., et al., Eur. J. Immunol. 25:952-957 (1995).
5. Hogervorst, E. J. M., et al. Eur. J. Immunol. 21:1289-1296 (1991)
6. Griffiths, M. M., et al., Arthritis Rheum. 36:254 (1993)
7. Van Eden, W., et al., Nature (Lond.) 331:171-173 (1988)
8. Holoshitz, J., et al., Science (Washington D.C.) 219:56-58 (1983)
9. Holoshitz, J., et al., Lancet 2:305-309 (1986)
10. Res, P. C. M., et al., Lancet 2:478-480 (1988)
11. Gaston, J. S. H., et al., J. Immunol. 143:2494-2500 (1984)
12. Gaston, J. S. H., et al., J. Exp. Med. 171:831-841 (1990)
13. Quayle, A. J., et al., Eur. J. Immunol. 22:1315-1322 (1992)
14. Henwood, J., et al., Eur. J. Immunol. 23:1256-1265 (1992)
15. Billingham, M. E. J., et al., J. Exp. Med. 171:339-344 (1990)
16. Hogervorst, E. J. M., et al., Int. Immunol. 4:719 (1992)
17. Young, X. D., et al., Clin. Exp. Immunol. 81:189-194 (1990)
18. Friedland, J. S., et al., Clin. Exp. Immunol. 91: 58-62 (1993)
19. Anderston, S. M., et al., J. Immunol. 152:3656-3664 (1994)
20. Moudgil, K. D., et al., J. Exp. Med. 185:1307-1316 (1997)
21. Jindal, S., et al., Mol. Cell. Biol. 9:2279-2283 (1989)
22. Kleinau, S. K., et al., Scand. J. Immunol. 33:195-202 (1991)
23. Munk, M. E., et al., J. Immunol. 143:2844 (1989)
24. Anderston, S. M., et al., Eur. J. Immunol. 23:33 (1993)
25. Shinnik, T., et al., Eur. J. Immunol. 22:1315-1322 (1992)

26. Kasprzyk, P. G., et al., Anal. Biochem. 174:224 (1988)
27. Warren, K. G., et al., Proc. Natl. Acad. Sci. USA 92:11061 (1995)
28. Elias, D., et al., Lancet 343:704-706 (1994)
29. Elias, D., et al., Diabetes 45:1168-1172 (1996)
30. Jordan, S. C. and Toyoda, M., Clin. Exp. Immunol. 97:31-38 (1994)
31. Chen, W., et al., J. Immunol 162:3212-3219 (1999)
32. Barker et al., Autoimmunity 14:73-77 (1992)
33. Ulmansky, R. et al., J. Immunol 168:6463-6469 (2002)
34. Steinitz, M. In: Immunoassay technology. R. S. Pal (ed.) Macmillan Press U.K. pp:1-17 (1988)

The invention claimed is:

1. A purified antibody directed against a purified peptide consisting of the amino acid sequence of SEQ ID: No. 1 or against biologically functional homologues and derivatives thereof, wherein the biologically functional homologues and derivatives thereof is selected from the group consisting of SEQ ID: No. 2 and SEQ ID: No. 3.

2. An antibody as claimed in claim 1, directed against a purified peptide consisting of the amino acid sequence of SEQ ID: No. 1.

3. A purified antibody directed against a purified peptide consisting of the amino acid sequence of SEQ ID: No. 2.

4. A purified antibody directed against a purified peptide consisting of the amino acid sequence of SEQ ID: No. 3.

5. A purified antibody directed against a purified peptide consisting of the amino acid sequence of SEQ ID: No. 4.

6. A composition for the passive immunization against an autoimmune or inflammatory disorder selected from the group consisting of type I diabetes and arthritis selected from the group consisting of: Adjuvant arthritis (AA), Collagen induced arthritis (CIA) and Rheumatoid arthritis (RA) consisting of a pharmaceutically effective amount of an antibody as claimed in claim 1, and a pharmaceutically-acceptable excipient.

7. A composition for significantly reducing disease severity of an autoimmune or inflammatory disorder selected from the group consisting of type I diabetes and arthritis selected from the group consisting of: Adjuvant arthritis (AA), Collagen induced arthritis (CIA) and Rheumatoid arthritis (RA), consisting of a pharmaceutically-effective amount of an antibody as claimed in claim 1 and a pharmaceutically-acceptable excipient.

8. A composition consisting of a pharmaceutically effective amount of an antibody as claimed in claim 1 that inhibits exacerbation of inflammatory or autoimmune diseases selected from the group consisting of type I diabetes and arthritis selected from the group consisting of: Adjuvant arthritis (AA), Collagen induced arthritis (CIA) and Rheumatoid arthritis (RA), and a pharmaceutically-acceptable excipient.

9. A composition for the passive immunization against an autoimmune or inflammatory disorder selected from the group consisting of type I diabetes and arthritis selected from the group consisting of: Adjuvant arthritis (AA), Collagen induced arthritis (CIA) and Rheumatoid arthritis (RA), consisting of a pharmaceutically effective amount of an antibody as claimed in claim 3, and a pharmaceutically-acceptable excipient.

10. A composition for significantly reducing disease severity of an autoimmune or inflammatory disorder selected from the group consisting of type I diabetes and arthritis selected from the group consisting of: Adjuvant arthritis (AA), Collagen induced arthritis (CIA) and Rheumatoid arthritis (RA), consisting of a pharmaceutically-effective amount of an antibody as claimed in claim 3 and a pharmaceutically-acceptable excipient.

11. A composition consisting of a pharmaceutically effective amount of an antibody as claimed in claim 3 that inhibits exacerbation of inflammatory or autoimmune diseases selected from the group consisting of type I diabetes and arthritis selected from the group consisting of: Adjuvant arthritis (AA), Collagen induced arthritis (CIA) and Rheumatoid arthritis (RA), and a pharmaceutically-acceptable excipient.

12. A method for significantly reducing disease severity of autoimmune and inflammatory disorders selected from the group consisting of type I diabetes and arthritis selected from the group consisting of adjuvant arthritis (AA), collagen-induced arthritis (CIA), and rheumatoid arthritis (RA) comprising the step of administering to a subject in need a therapeutically effective amount of at least one antibody as claimed in claim 1 or a composition comprising the same, capable of inhibiting exacerbation of said autoimmune and inflammatory disorders, thereby significantly reducing disease severity.

13. A method for passive immunization against an autoimmune or inflammatory disease selected from the group consisting of type I diabetes and arthritis selected from the group consisting of adjuvant arthritis (AA), collagen-induced arthritis (CIA), and rheumatoid arthritis (RA) of a subject in need, comprising the step of administering an immunologically effective amount of at least one antibody as claimed in claim 1 or a composition comprising the same.

* * * * *

SEQUENCE LISTING

```
<160> NUMBER OF SEQ ID NOS: 5

<210> SEQ ID NO 1
<211> LENGTH: 22
<212> TYPE: PRT
<213> ORGANISM: Mycobacterium tuberculosis

<400> SEQUENCE: 1

Gly Pro Lys Gly Arg Asn Val Val Leu Glu Lys Lys Trp Gly Ala Pro
1               5                   10                  15

Thr Ile Thr Asn Asp Gly
            20

<210> SEQ ID NO 2
<211> LENGTH: 16
<212> TYPE: PRT
<213> ORGANISM: Mycobacterium tuberculosis

<400> SEQUENCE: 2

Gly Pro Lys Gly Arg Asn Val Val Leu Glu Lys Lys Trp Gly Ala Pro
1               5                   10                  15

<210> SEQ ID NO 3
<211> LENGTH: 16
<212> TYPE: PRT
<213> ORGANISM: Mycobacterium tuberculosis

<400> SEQUENCE: 3

Val Val Leu Glu Lys Lys Trp Gly Ala Pro Thr Ile Thr Asn Asp Gly
1               5                   10                  15

<210> SEQ ID NO 4
<211> LENGTH: 20
<212> TYPE: PRT
<213> ORGANISM: Rattus norvegicus

<400> SEQUENCE: 4

Thr Val Ile Ile Glu Gln Ser Trp Gly Ser Pro Lys Val Thr Lys Asp
1               5                   10                  15

Gly Val Thr Val
            20

<210> SEQ ID NO 5
<211> LENGTH: 67
<212> TYPE: DNA
<213> ORGANISM: Mycobacterium tuberculosis

<400> SEQUENCE: 5
gccgccatgg gaccaaaggg acgcaacgtg gtactagaga agaaatgggg cgcgccgtag    60
ctcgaga                                                              67
```